(12) United States Patent
Boehlke et al.

(10) Patent No.: US 8,834,493 B2
(45) Date of Patent: Sep. 16, 2014

(54) DEVICE AND METHOD FOR VASCULAR CLOSURE

(75) Inventors: Raimar Boehlke, Chanhassen, MN (US); Kedar R. Belhe, Minnetonka, MN (US); Catherine A. Pipenhagen, Chanhassen, MN (US)

(73) Assignee: St. Jude Medical, Cardiology Division, Inc., Minnetonka, MN (US)

(*) Notice: Subject to any disclaimer, the term of this patent is extended or adjusted under 35 U.S.C. 154(b) by 513 days.

(21) Appl. No.: 11/551,523

(22) Filed: Oct. 20, 2006

(65) Prior Publication Data

US 2008/0097479 A1    Apr. 24, 2008

(51) Int. Cl.
*A61B 17/04* (2006.01)

(52) U.S. Cl.
CPC ......... *A61B 17/0469* (2013.01); *A61B 17/0482* (2013.01); *A61B 2017/0475* (2013.01); *A61B 2017/0474* (2013.01); *A61B 2017/0454* (2013.01); *A61B 2017/0458* (2013.01); *A61B 2017/0472* (2013.01); *A61B 2017/047* (2013.01); *A61B 2017/0496* (2013.01); *A61B 17/0487* (2013.01); *A61B 2017/0477* (2013.01)
USPC .......................................... 606/144; 606/148

(58) Field of Classification Search
USPC ................... 606/144, 139, 148, 232, 145–147
See application file for complete search history.

(56) References Cited

U.S. PATENT DOCUMENTS

| | | | |
|---|---|---|---|
| 5,084,058 A | 1/1992 | Li | |
| 5,324,298 A * | 6/1994 | Phillips et al. | 606/148 |
| 5,364,408 A | 11/1994 | Gordon | |
| 5,374,275 A * | 12/1994 | Bradley et al. | 606/144 |
| 5,403,329 A * | 4/1995 | Hinchcliffe | 606/147 |
| 5,458,609 A * | 10/1995 | Gordon et al. | 606/144 |
| 5,496,348 A | 3/1996 | Bonnuti | |
| 5,527,321 A * | 6/1996 | Hinchliffe | 606/144 |
| 5,562,684 A | 10/1996 | Kammerer | |
| 5,643,292 A | 7/1997 | Hart | |
| 5,797,928 A * | 8/1998 | Kogasaka | 606/144 |
| 5,845,645 A | 12/1998 | Bonutti | |
| 5,868,762 A * | 2/1999 | Cragg et al. | 606/144 |

(Continued)

FOREIGN PATENT DOCUMENTS

| | | |
|---|---|---|
| WO | 2004073527 A1 | 9/2004 |
| WO | 2005112789 A2 | 12/2005 |

OTHER PUBLICATIONS

International Search Report, PCT/US2007/022239, mailed Apr. 7, 2008.

*Primary Examiner* — Dianne Dornbusch
*Assistant Examiner* — Alexander Orkin
(74) *Attorney, Agent, or Firm* — Holland & Hart

(57) ABSTRACT

A vascular closure delivery system is provided comprising a needle and suture delivery unit and a suture knot system. The delivery unit may comprise a tube, a leg, a tensioning device, a pusher, a needle, and an actuator, the tube being configured to house the needle. In an open position, the tensioning device exerts tension on the leg, and the pusher and suturing apparatus are in a delivery configuration for delivering the needle to the internal tissue wall. Further, actuation of the actuator moves the pusher towards an expulsion end of the tube such that the pusher engages the needle and expels the needle from the tube. The suture knot system comprises a shaft, an inner tubular member, and an inner rod. The inner tubular member is radially translatable with respect to the shaft. The inner rod is slidably coupled to and is axially translatable within the inner tubular member.

20 Claims, 34 Drawing Sheets

(56) References Cited

U.S. PATENT DOCUMENTS

| | | | |
|---|---|---|---|
| 5,984,933 A | 11/1999 | Yoon | |
| 5,993,459 A | 11/1999 | Larsen et al. | |
| 6,059,800 A | 5/2000 | Hart et al. | |
| 6,074,395 A | 6/2000 | Trott et al. | |
| 6,132,439 A * | 10/2000 | Kontos | 606/139 |
| 6,136,010 A * | 10/2000 | Modesitt et al. | 606/144 |
| 6,283,947 B1 | 9/2001 | Mirzaee | |
| 6,358,258 B1 * | 3/2002 | Arcia et al. | 606/139 |
| 6,358,259 B1 * | 3/2002 | Swain et al. | 606/148 |
| 6,533,795 B1 | 3/2003 | Tran et al. | |
| 6,702,825 B2 | 3/2004 | Frazier et al. | |
| 6,716,224 B2 | 4/2004 | Singhatat | |
| 6,743,241 B2 * | 6/2004 | Kerr | 606/144 |
| 6,855,124 B1 | 2/2005 | Gonzalez et al. | |
| 6,896,685 B1 * | 5/2005 | Davenport | 606/144 |
| 6,939,357 B2 * | 9/2005 | Navarro et al. | 606/145 |
| 7,160,309 B2 | 1/2007 | Voss | |
| 7,226,467 B2 | 6/2007 | Lucatero et al. | |
| 2003/0040712 A1 | 2/2003 | Ray et al. | |
| 2003/0181926 A1 | 9/2003 | Dana et al. | |
| 2004/0068273 A1 | 4/2004 | Fariss et al. | |
| 2004/0097973 A1 | 5/2004 | Loshakove et al. | |
| 2005/0159812 A1 | 7/2005 | Dinger et al. | |
| 2005/0182427 A1 * | 8/2005 | Manzo | 606/144 |
| 2006/0030868 A1 | 2/2006 | Bennett | |
| 2007/0203507 A1 * | 8/2007 | McLaughlin et al. | 606/144 |
| 2007/0213757 A1 * | 9/2007 | Boraiah | 606/184 |
| 2008/0033459 A1 | 2/2008 | Shafi et al. | |
| 2008/0097480 A1 | 4/2008 | Schorr et al. | |
| 2008/0097481 A1 | 4/2008 | Schorr et al. | |
| 2008/0097484 A1 | 4/2008 | Lim et al. | |
| 2008/0097527 A1 | 4/2008 | Lim et al. | |

* cited by examiner

DEVICE AND METHOD FOR VASCULAR CLOSURE

FIELD OF THE INVENTION

The present invention generally relates to a vascular closure delivery system and, more specifically, to a vascular closure delivery system for deploying needles and sutures for suturing internal tissue walls.

BACKGROUND OF THE INVENTION

Various medical procedures, particularly cardiology procedures, involve accessing a corporeal vessel through the formation of a hole or opening in the vessel wall so that a medical procedure can be performed. After the particular medical procedure has been performed, the access hole in the vessel wall must be closed. A number of prior vascular closure devices and methods have been developed in attempting to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. No. 5,643,292 and U.S. Pat. No. 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use. Furthermore, many suturing devices dilate the vessel opening and perform the medical procedure via the vessel opening before the suture is extended across the vessel opening for approximation tissue surrounding the vessel wall.

In many prior art systems, needle deployment is done manually by a physician or operator. Manual deployment involves estimation by the operator of how the needle should be deployed, how fast the trigger for the needle should be actuated, how much force should be applied, etc. The manual method of needles deployment require the physician to manually pull a lever or button proximally to deploy the needles. The speed or force used to actuate the lever or button will determine the force the needle will have when penetrating the artery. The more force the needle have in penetrating the artery the greater the possibility of piercing an artery. Thus, the physician must exert sufficient force to penetrate the artery but take care not to exert so much force as to pierce the artery. Manual deployment allows for greater inconsistency and user error as different physicians have differing perception when it comes to how much force or speed to apply when using a device. It would be advantageous to have a device for automated needle deployment that reduces operator estimation and, thus, operator error, and standardizes deployment of the needle.

Typically, the suture securing the hole in the vessel wall is closed using a sliding knot. The knot can be slid along the suture. Thus, the surgical site is contacted with a sliding suture when the knot is pushed or cinched down and thus causes movement of the suture at the tissue site. Tying of the suture with an over hand suture loop enables sliding of the knot while the suture at the tissue site remains stationary. A device for transporting two or more over hand suture loops to percutaneous surgical site thus would also be useful.

BRIEF SUMMARY OF THE INVENTION

A vascular closure delivery system for closing a tissue wall opening is provided.

In one embodiment, the vascular closure delivery system comprises a suturing apparatus and suture delivery unit and a suture knot system. The suturing apparatus and suture delivery unit comprises at least one tube, at least one leg, a tensioning device, a pusher, a suturing apparatus, and an actuator. The at least one tube is configured to house the pusher and the suturing apparatus and has an expulsion end. The at least one leg has a first end and a second and is coupled to the at least one tube proximate the first end of the leg. The tensioning device is coupled to the at least one leg proximate the second end of the leg. The pusher has a suturing apparatus engaging end and is slidably disposed within the tube. The suturing apparatus has a sharp end and an opposite end and is slidably disposed within the tube. A suture is associated with the suturing apparatus. The actuator is operatively associated with the pusher. When the at least one leg is in an open position, the tensioning device exerts tension on the leg such that the leg is movably suspended and can move with respect to the tensioning device, and the pusher and suturing apparatus are in an delivery configuration for delivery of the suturing apparatus to the internal tissue wall. Further, actuation of the actuator moves the pusher towards the expulsion end of the tube such that the suturing apparatus engaging end of the pusher engages the suturing apparatus and expels the suturing apparatus from the tube. The suture knot system comprises a shaft, an inner tubular member, and an inner rod. The shaft has a proximal end and a distal end. The inner tubular member has a proximal end and a distal end and is provided within the shaft. The inner tubular member is radially translatable with respect to the shaft. The inner rod has a proximal end and a distal end and is provided within the inner tubular member. The inner rod is slidably coupled to the inner tubular member and is axially translatable within the inner tubular member.

Other features and advantages of the invention will become apparent from the following detailed description, taken in conjunction with the accompanying drawings which illustrate, by way of example, various features of embodiments of the invention.

DETAILED DESCRIPTION OF THE INVENTION

A vascular closure delivery system that may be used to deliver needles and sutures for closing internal tissue walls after a medical procedure is performed through a vascular wall opening is provided. Tissue that may be closed in accordance with the teachings herein may be part of a lumen such as a blood vessel, body cavity, other organ, or any tissue suitable for suturing.

Figure 1:
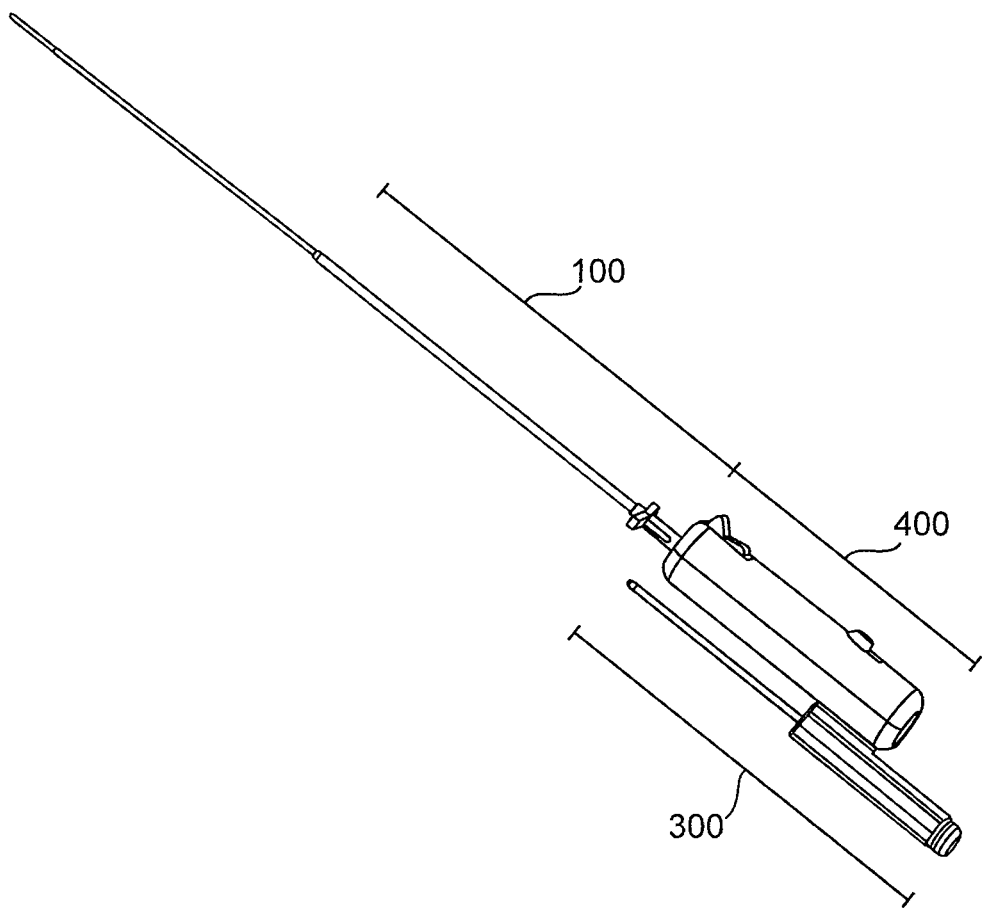
FIG. 1 illustrates a vascular closure delivery system including a needle and suture delivery unit in accordance with one embodiment.
Figure 2A:
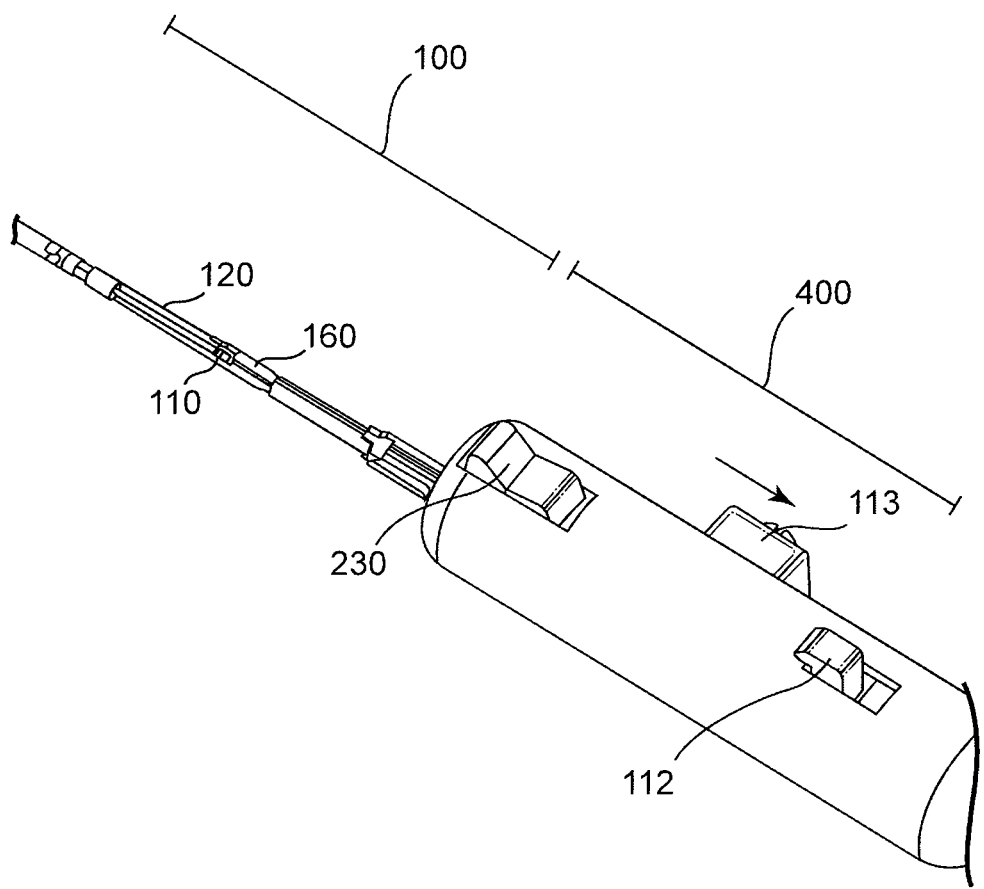
FIG. 2a illustrates the vascular closure delivery system of FIG. 1 in a closed configuration.
Figure 2B:
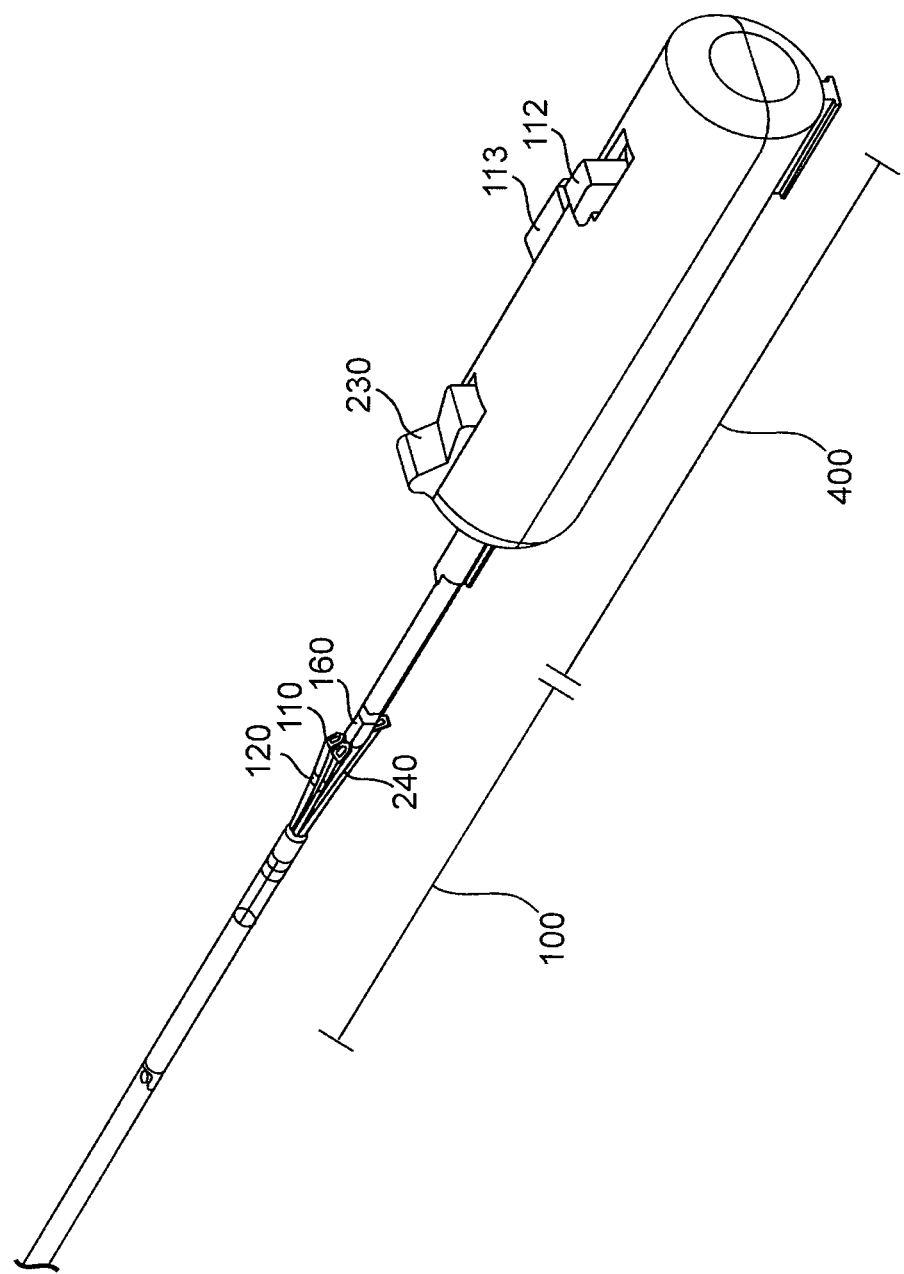
FIG. 2b illustrates the vascular closure delivery system of FIG. 1 in a partially open configuration.
Figure 2C:
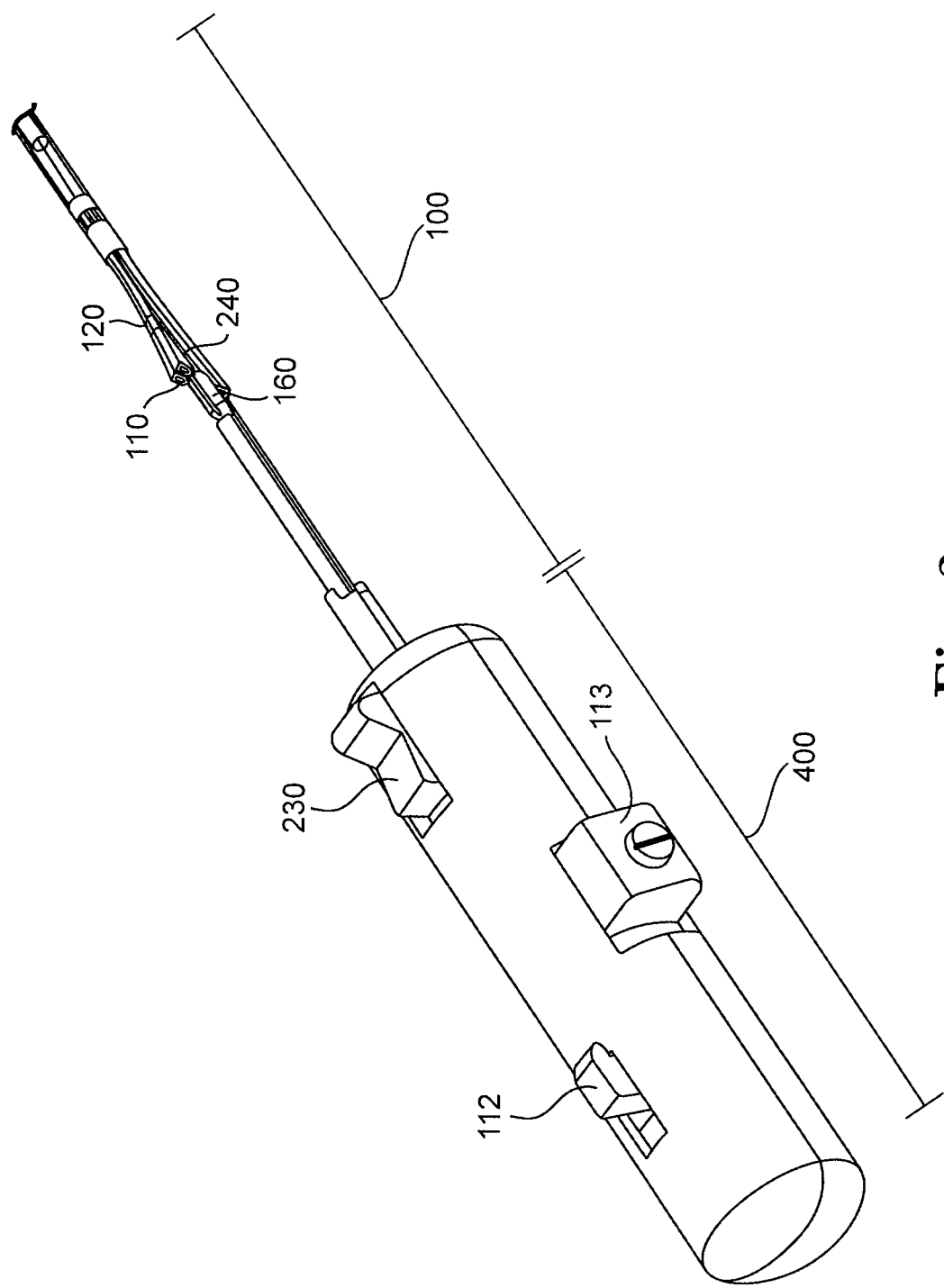
FIG. 2c illustrates the vascular closure delivery system of FIG. 1 in an open configuration.
Figure 2D:
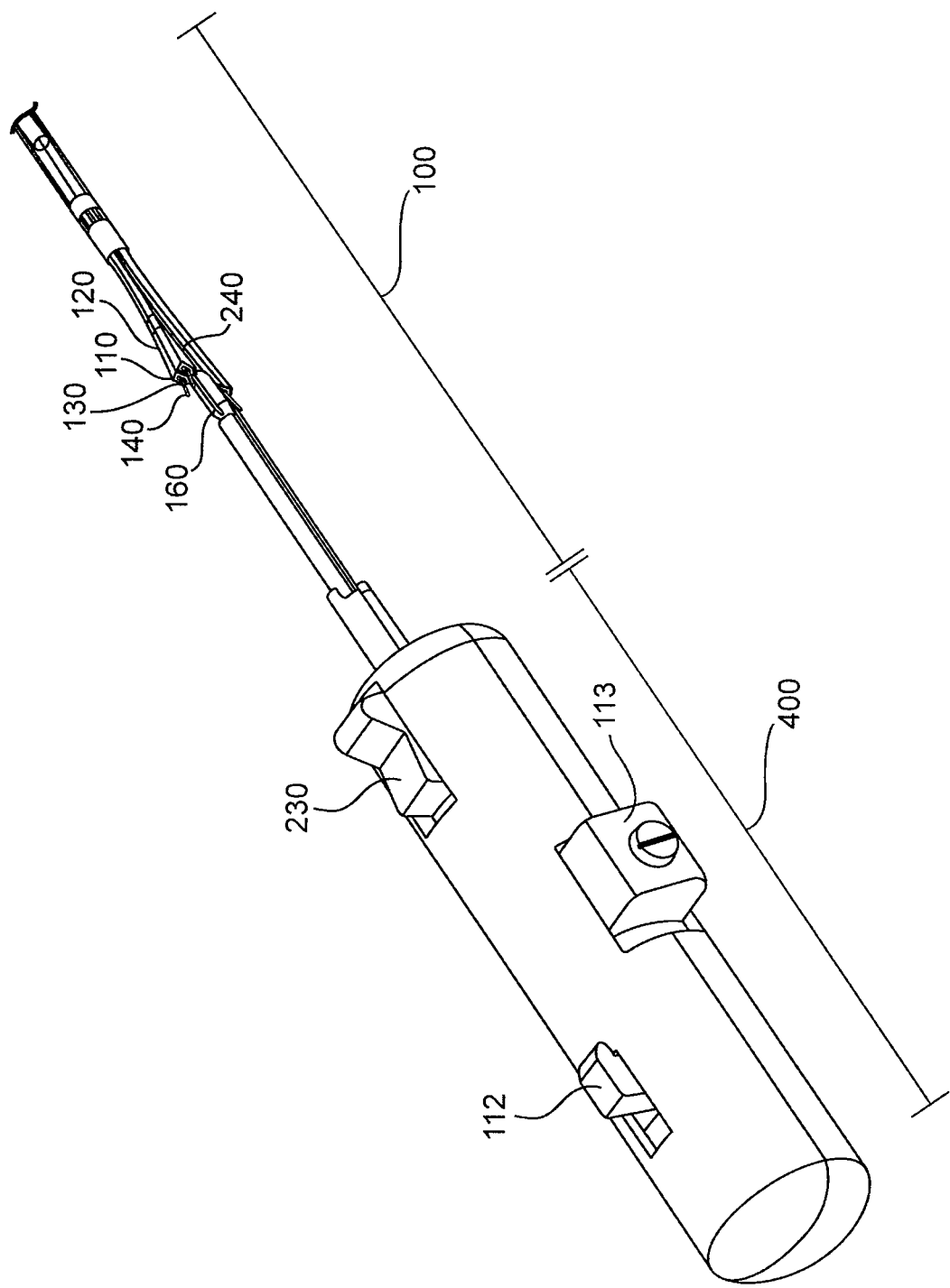
FIG. 2d illustrates the vascular closure delivery system of FIG. 1 in a needle deploying configuration.

FIG. 1 illustrates one embodiment of the vascular closure delivery system. As shown, the vascular closure delivery system may include a handle 400, a needle and suture delivery unit 100, and a suture knot system 300. FIGS. 2a-2d illustrate one embodiment of a vascular closure delivery system comprising a handle and needle and suture delivery unit 100. FIG. 2a illustrates the needle and suture delivery unit in a closed configuration, FIGS. 2b and 2c illustrates the needle and suture delivery unit in a partially open and an open configuration, respectively, and FIG. 2d illustrates the needle and suture delivery unit in a needle deploying configuration. The handle 400 of the embodiment of FIGS. 1 and 2a-2d is an automatic handle wherein needle deployment is automatic through actuation of a control, such as a push button.

Referring to FIGS. 2a-2d, the needle and suture delivery unit 100 includes one or more legs 110, needle carrier tubes 120, pushers 130, needles 140, and sutures 150 (see FIG. 5), and is disposed at a distal end of the vascular closure delivery system. Generally, each leg 110 may be coupled at one end to a support 160 and one or more tensioning cables, and optionally may be coupled at another end to a needle delivery tube 120. The legs 110 may be actuated to an open operational configuration for deploying the needles 140. The needles 140 and sutures 150 may be delivered to the intima of an artery and may out pass the exterior wall such as the femoral artery. The needle and suture delivery unit 100 is insertable into tissue, such as the artery, so that one or more needles and sutures may be delivered to the internal tissue of the patient. A tube or sheath may be provided and may serve as a cover for all or a portion of the needle and suture delivery unit 100. The sheath may be pulled back or peeled away to expose some or all of the needle and suture delivery unit.

The handle 400 of the vascular closure delivery system is provided at a proximal end thereof and may be used to control the needle and suture delivery unit 100. In the embodiment of FIGS. 2a-2d, the handle 400 includes first, second, and third actuators, 113, 112, and 230. The first actuator 113 may be actuated to move the leg 110 from a collapsed configuration to an open, operational configuration. The second actuator 112 may be actuated to deploy the needle 140 via deployment of the pusher 130. The third actuator 230 may be used to return the pusher 130 to its original configuration. The first actuator 113 may then be released to return the leg 110 to the collapsed configuration.

Figure 3A:
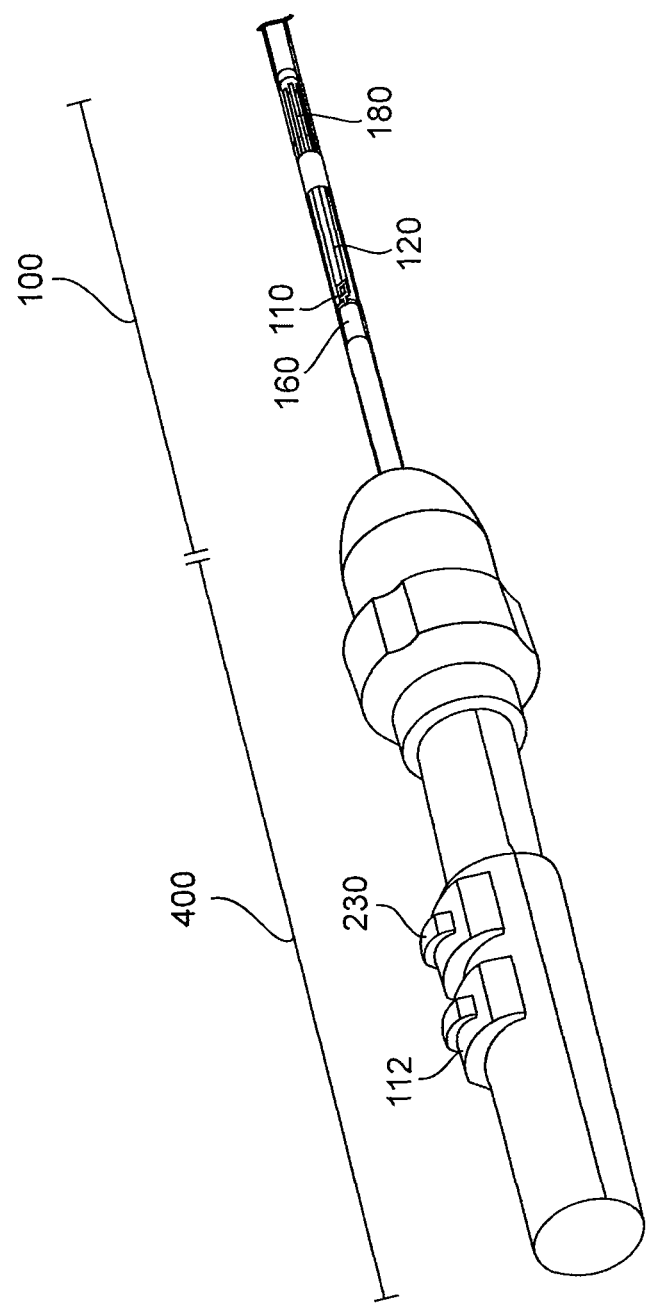
FIG. 3a illustrates a vascular closure delivery system including a needle and suture delivery unit, the needle and suture delivery unit being in a closed configuration in accordance with one embodiment.
Figure 3B:
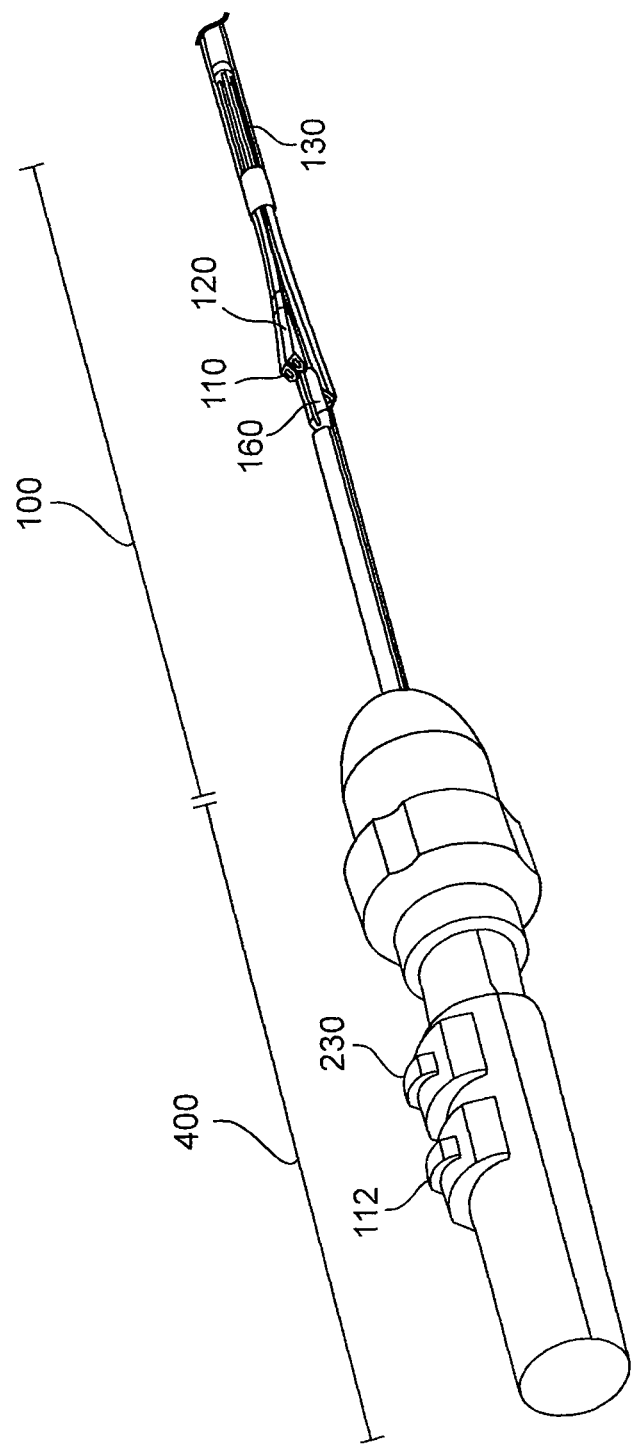
FIG. 3b illustrates the vascular closure delivery system of FIG. 3a in an open configuration.
Figure 3C:
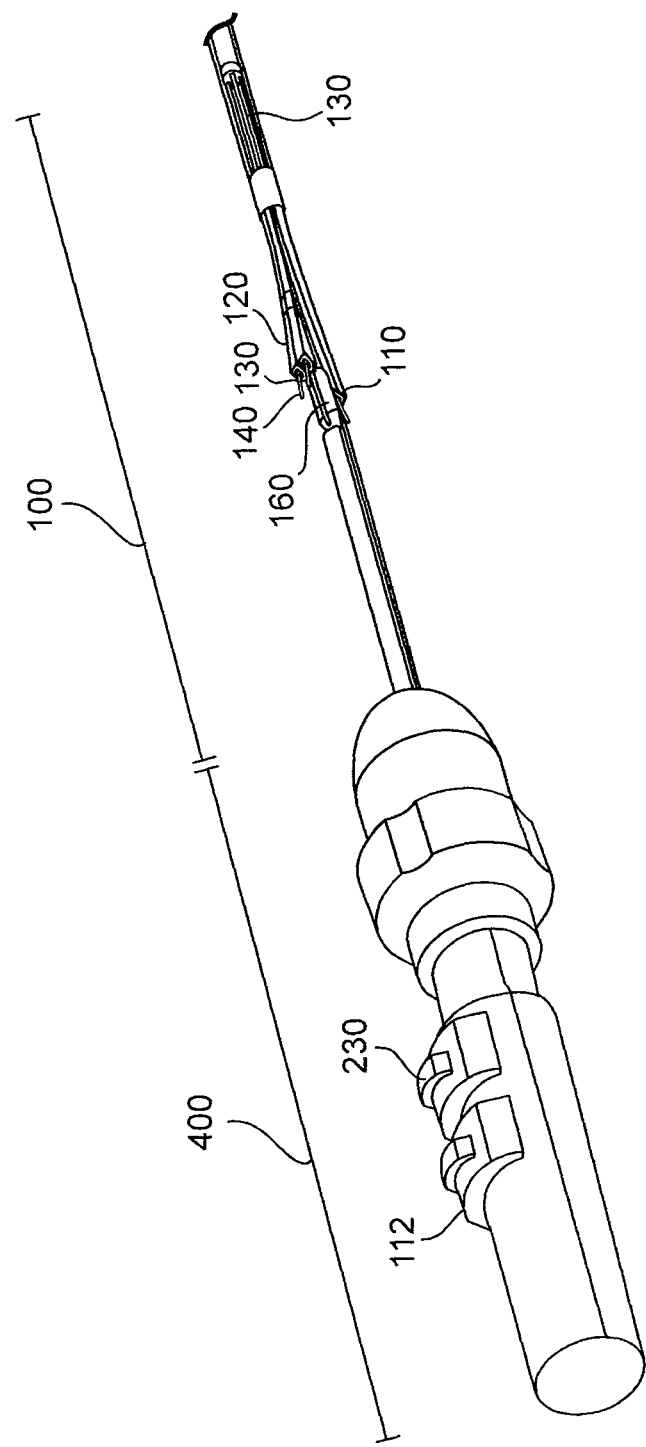
FIG. 3c illustrates the vascular closure delivery system of FIG. 3a in a needle deploying configuration.

FIGS. 3a-3c illustrate an alternative embodiment of a handle 400 and needle and suture delivery unit 100 of the vascular closure delivery system. FIG. 3a illustrates the needle and suture delivery unit in a closed configuration, FIG. 3b illustrates the needle and suture delivery unit in an open configuration, and FIG. 3c illustrates the needle and suture delivery unit in a needle deploying configuration. The needle and suture delivery unit 100 of FIGS. 3a-3c is substantially the same as the needle and suture delivery unit 100 of FIGS. 1 and 2a-2d and reference is made to the description thereof. The handle 400 of FIGS. 3a-3c is a manual deployment handle wherein the needle deployment is manual—for example, via a pull button that is pulled proximally to deploy the needles. The handle 400 includes two actuators 112 and 230.

It is to be noted that in alternative embodiments, more or fewer sets of legs, pushers, needles, and sutures may be used. Further, the number of legs, pushers, needles, and sutures may not be equal. Reference to distal and proximal positions may be made herein. Generally, proximal refers to towards the physician or operator and distal refers to towards the patient. Such reference is for the purposes of illustration only and is not intended to be limiting, and orientations of the various components may be altered.

Figure 4:
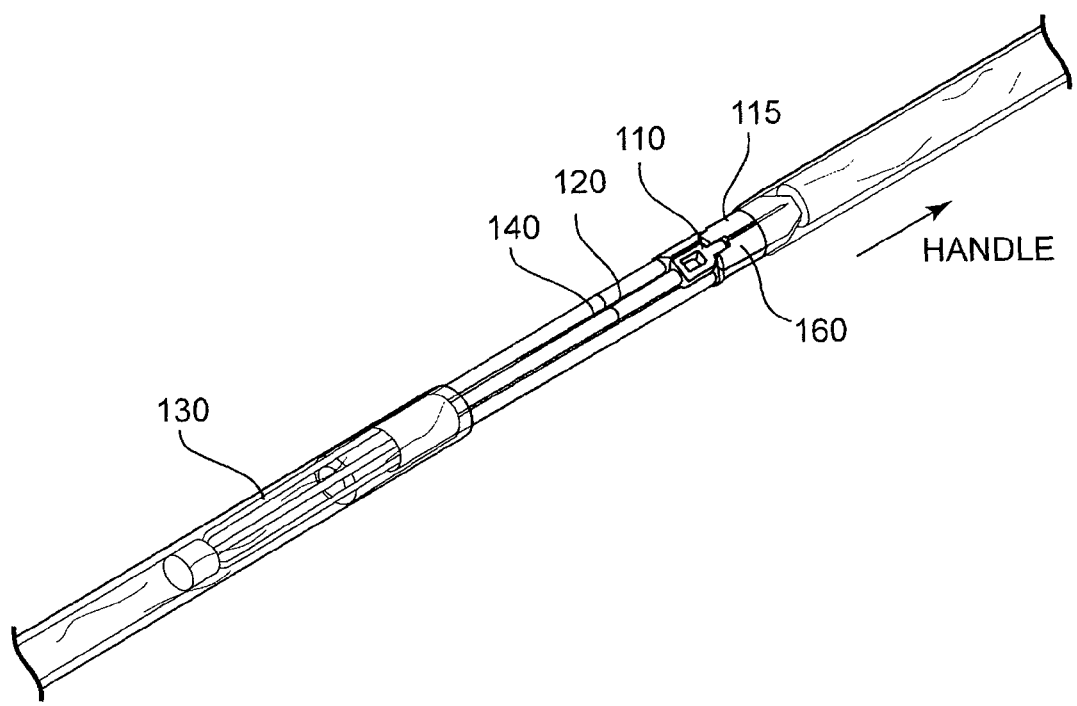
FIG. 4 illustrates a needle and suture delivery unit of the vascular closure delivery system, the needle and suture delivery unit being in a closed configuration, in accordance with one embodiment.
Figure 5:
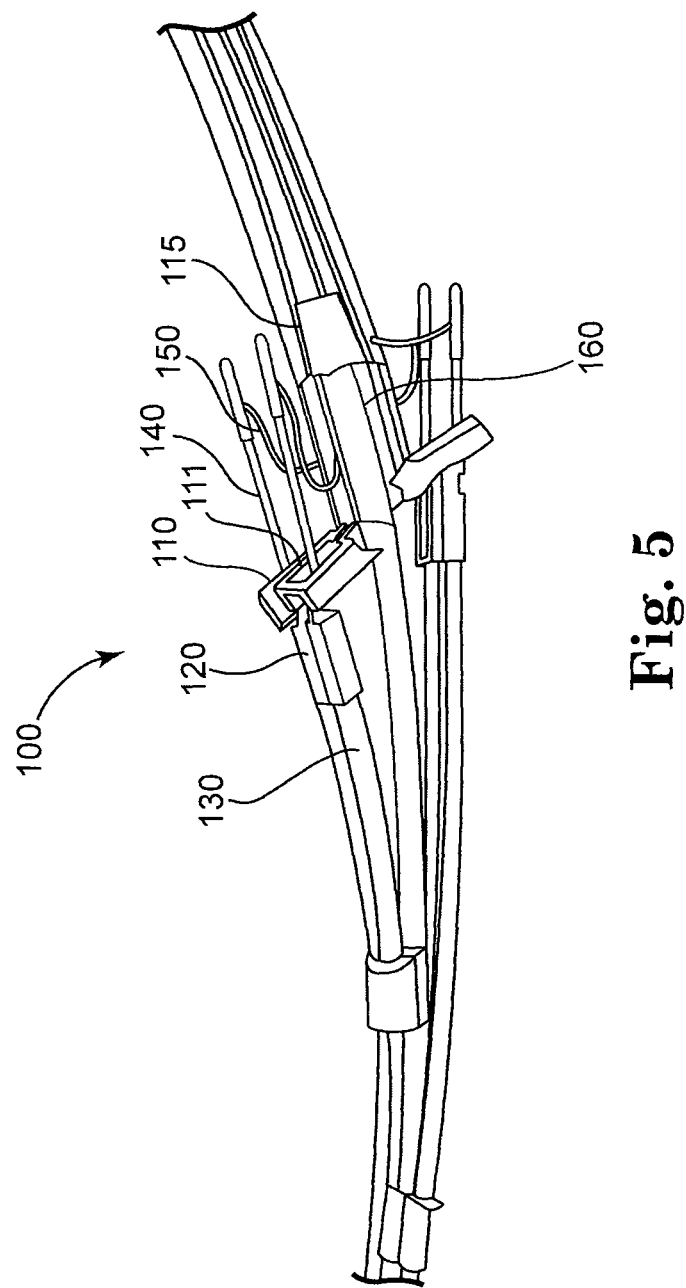
FIG. 5 illustrates a needle and suture delivery unit of the vascular closure delivery system, the needle and suture delivery unit being in a needle deploying configuration, in accordance with one embodiment.
Figure 6:
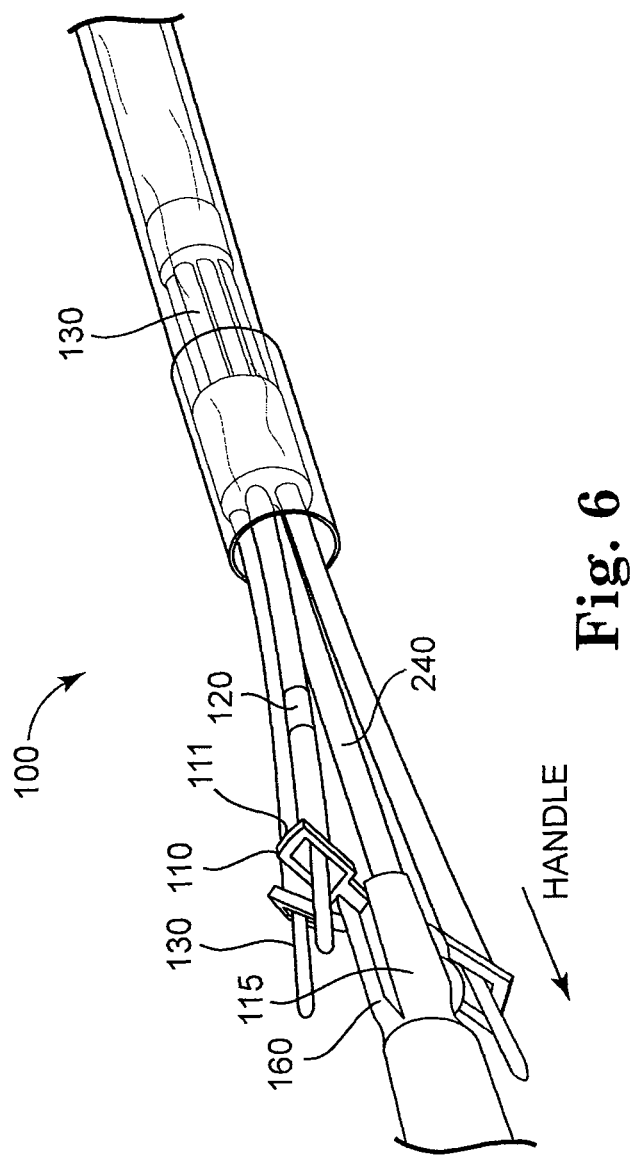
FIG. 6 illustrates a needle and suture delivery unit of the vascular closure delivery system, the needle and suture delivery unit being in a needle deploying configuration, in accordance with one embodiment.

FIGS. 4-6 illustrate the needle and suture delivery unit 100 in accordance with one embodiment. FIG. 4 illustrates the needle and suture delivery unit 100 in a closed configuration while FIGS. 5 and 6 illustrate the needle and suture delivery unit 100 in and open, needle deploying configuration. The leg 110 of the needle and suture delivery unit 100 serves as a guide for the needle carrier tube 120. More specifically, the leg 110 moves the needle carrier tube 120 from the closed configuration shown in FIGS. 2a, 3a, and 4 to the open configuration shown in FIGS. 2c and 3b such that the pusher 130 may expel the needle 140 from the needle carrier tube 120, as shown in FIGS. 2d, 3c, 5 and 6. In one embodiment, the legs 110 are moved to an open position by deploying a pull force on the first actuator 113 of the handle 400. As shown in FIGS. 2a-2d, the first actuator 113 may be a lever. The pull force pulls the needle carrier tubes 120 proximally, thereby pulling the tubes 120 and legs 110 from their collapsed state to an operational and open position. Tactile feedback may indicate to the user to stop applying pull force when the legs 110 have opened. In the open position, the legs 110 are generally at an angle to the support 160 of approximately 30 degrees to approximately 70 degrees and are flexibly suspended via a tensioning device which may be located at the handle 400.

With the leg 110 in an open configuration, the needle and suture delivery unit 100 is ready to deploy the needle 140 and suture 150. Delivery of the needle 140 may be done by actuating the second actuator 112 on the handle 400. The second actuator deploys the pusher 130 towards an expulsion end of the needle carrier tube 120. The pusher 130 in turn expels the needle 140 from the needle carrier tube 120.

As can be seen in FIG. 4, the needle carrier tube 120 is coupled to the leg 110. More specifically, in the embodiment shown, the tube 120 is hinged to the leg 110. The support 160 supports the leg 110, which in turn supports the tube 120. In the closed configuration, shown in FIGS. 2a, 3a, and 4, both the tube 120 and the leg 110 are aligned generally parallel to the support 160. In an area proximal to the support 160, the leg 110 is also coupled to a cable 115 which serves to actuate the leg 110 from a closed position to an open position, and vice versa. The cable 115 may be referred to as a tensioning cable.

Pushers 130 and needles 140 of the needle and suture delivery unit 100 may be slidably disposed within the needle carrier tube 120. The needle carrier tube 120 may have any suitable cross section such as a circular cross section or a square cross section. The needle carrier tube 120 has a needle expulsion end from which the needle 140 is expelled to deploy the needle 140 and suture 150. The needle expulsion end may be the distal end of the needle or the proximal end of the needle in various embodiments. In the embodiments shown, the needle expulsion end of the needle carrier tube 120 is the proximal end of the needle carrier tube 120. The pusher 130 likewise has a needle engagement end. The needle engagement end of the pusher 130 is the end of the pusher 130 that engages the needle 140 to expel the needle 140 from the needle carrier tube 120. The pusher 130 may be grounded and/or the needle engagement end of the pusher 130 may have adaptive features to enable coupling with the needle, described more fully below. The needle engagement end of the pusher 130 may be the proximal end of the pusher or the distal end of the pusher in various embodiments. In the embodiments shown, the needle engagement end of the pusher 130 is the proximal end of the pusher 130. Thus, the needle engagement end of the pusher 130 engages the needle 140 to expel the needle 140 from the needle expulsion end of the needle carrier tube 120. More specifically, in the embodiments shown, the proximal end of the pusher 130 engages the needle 140 to expel the needle 140 proximally from the proximal end of the needle carrier tube 120. FIGS. 5 and 6 illustrate the needle and suture delivery unit 100 in a needle deploying configuration with the pusher 130 extending from the needle carrier tube 120, thus expelling the needle 140 therefrom.

Thus, in embodiments where the pusher 130 and needle 140 are provided in a needle carrier tube 120, the pusher 130 expels the needle 140 from the needle carrier tube 120. In one embodiment, where the sharp end of the needle 140 is situated for engagement with the needle engagement end of the pusher 130, the needle 140 is delivered from the needle carrier tube 120 sharp end last. This results in the needle 140 engaging with tissue only after it is fully delivered from the needle carrier tube 120. In another embodiment, as shown in FIGS. 4-6, the needle 140 is positioned in the carrier tube 120 such that the sharp end of the needle 140 is oriented toward the needle expulsion end of the carrier tube 120 and the opposite end of the needle 140 is oriented toward the needle engagement end of the pusher 130. In this embodiment, the needle 140 is delivered from the needle carrier tube 120 sharp end-first. Once the needle 140 engages with tissue, such as engaging the outside of an artery, it is substantially prevented from reentering the needle carrier tube 120.

The pusher 130 may have any suitable configuration. As previously discussed, the needle engagement end of the pusher 130 may have adaptive features to enable the needle engagement end of the pusher 130 to engage the needle 140 or to couple with the needle 140. In the embodiments shown, the pusher 130 comprises a rod-like structure wherein the needle engagement end of the pusher 130 is configured to be received by the opposite end of the needle 140 such that the needle 140 is carried by the pusher 130. The pusher 130 may be solid or hollow or a combination thereof. In the embodiment shown, the pusher 130 has a generally circular cross section. In other embodiments, the cross section of the pusher 130 may be varied. The pusher 130 is configured for movement towards the expulsion end of the needle carrier tube 120. Thus, the pusher 130 may be positioned in the needle carrier tube 120 for movement towards the needle expulsion end of the needle carrier tube 120 to expel the needle 140 therefrom. In one embodiment, such movement is in response to a springing action exerted on the pusher 130, either directly or indirectly such as via an actuating member, triggered by the actuator 113 of the handle 400, described more fully below. The combination of the length of the pusher 130 and the distance the pusher 130 moves may result in the needle engagement end of the pusher 130 moving through and out of the needle carrier tube 120. In some embodiments, the pusher 130 may exit the needle carrier tube 120 partially or not at all so long as the needle 140 is expelled from the needle carrier tube 120. As previously noted, the needle engagement end of the pusher 130 may be the distal end of the pusher 130 or the proximal end of the pusher 130.

Figure 7:
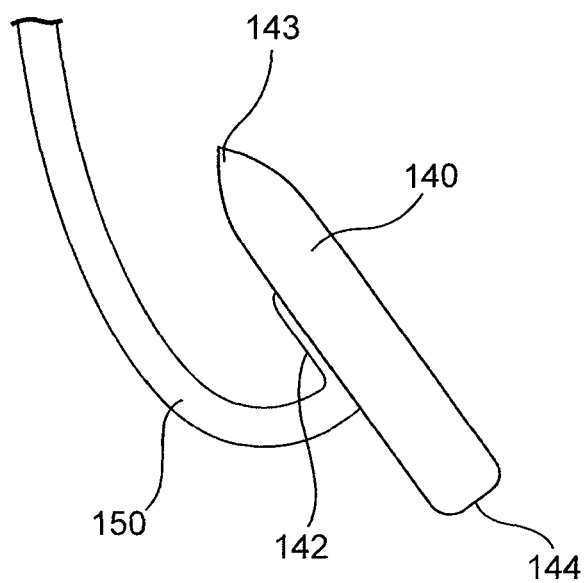
FIG. 7 illustrates a needle and suture for use with the vascular closure delivery system in accordance with one embodiment.
Figure 8:
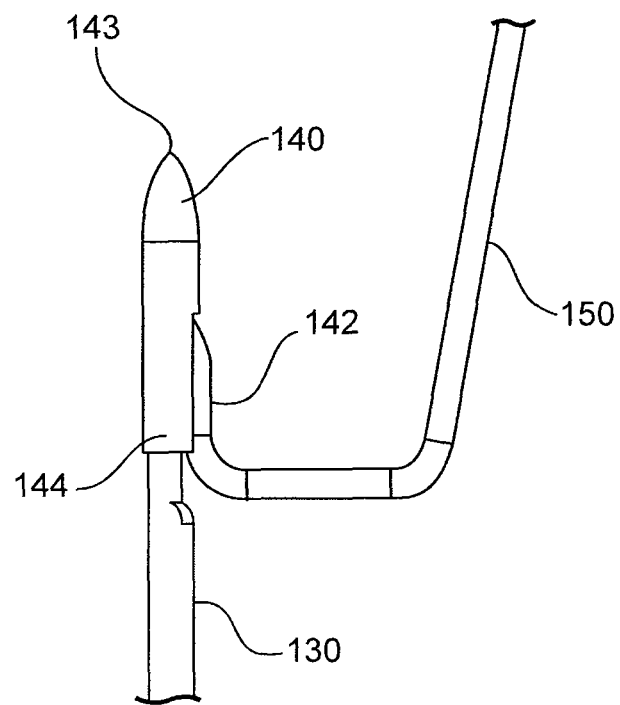
FIG. 8 illustrates a needle and suture for use with the vascular closure delivery system in accordance with one embodiment.

The needle 140 may be constructed of implantable stainless steel, a dissolvable polymer, or other material suitable for engaging with tissue. FIGS. 7 and 8 illustrate one embodiment of a needle 140 for use with the needle and suture delivery unit of the vascular closure delivery system. As shown, the needle 140 includes a sharp end 143 and an opposite end 144, the face of the opposite end 144 extending at an angle to a central axis of the needle 140. In one embodiment, the face of the opposite end 144 may be extend substantially perpendicular to the central axis of the needle 140. In alternative embodiments, the opposite end 144 may have different configurations. A slot 142 is provided along the needle body between the sharp end 143 and the opposite end 144. The slot 142 may fully extend to the opposite end 144. In the embodiment shown, the opposite end 144 of the needle 140 comprises a toggling edge. After the pusher 130 has expelled the needle 140 from the needle carrier tube 120 and begins to retract (described below), the toggle end 144 of the needle 140 contacts outside tissue of the artery. Such contact forces the needle 140 to push from the pusher 130. The toggle end 144 allows the needle 140 to fall from the pusher 130 upon contacting a barrier such as tissue of the artery. In alternative embodiments, other configurations of needles 140 may be used. Further, anchors other than a needle may be provided for placing the suture 150. For example, a pronged projectile or other suitably shaped projectile for engaging with tissue may be provided.

The suture 150 may be associated with or coupled to the needle 140 in any suitable manner and at any suitable location. For example, the suture 150 may be threaded through the needle 140, adhered to the needle 140, crimped to the needle 140, or other. In the embodiment of FIGS. 7 and 8, the suture 150 is crimped to the needle 140 generally between the sharp end 143 and the opposite end 144. More specifically, the suture 150 is coupled to the needle 140 in the slot 142 such that the suture 150 extends towards the opposite end 144 of the needle 140 in the slot 142. The suture 150 is thus hidden during piercing of the tissue with the needle 140 FIG. 8 illustrates the needle 140 as positioned relative to the pusher 130 before deployment of the needle 140 from the needle carrier tube 120. FIG. 8 further illustrates the suture 150. As shown, the suture 150 extends transversely from the slot 142 and towards the sharp end 143 of the needle 140. After needle 140 deployment, the orientation of the suture 150 with respect to the needle 140 may change as the suture 150 extends through the slot.

The suture 150 of the needle and suture delivery unit 100 may be composed of a variety of materials such as nylon, a bio-resorbable polymer, metal, or any suitable resorbable or nonresorbable suture material. In some embodiments, the suture may be a braided suture. One or more sutures 150 may be disposed on each needle 140 or other projectile of the needle and suture delivery unit 100. Thus, at least one end of the suture 150 is coupled to a needle 140. In the embodiment shown in FIGS. 1 and 2a-2c, the length of the suture is of a length such that the suture 150 extends from the needle 140 as engaged with the tissue, out of the tissue of the patient, to the suture knot system 300. A portion of the suture 150 may be disposed in the needle carrier tube 120, trailing from the needle 140, before the needle 140 is delivered to tissue.

Figure 9:
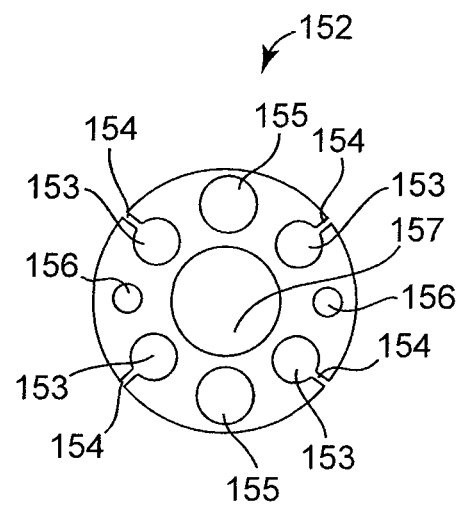
FIG. 9 illustrates a suture management lumen device for use with the vascular closure delivery system in accordance with one embodiment.

As shown in FIG. 9, the suture may be provided in a suture management lumen device 152. The suture management lumen device 152 may be used for suture storage and permits easy removal of suture. The suture management lumen device 152 protect the sutures during insertion of the needle and suture delivery unit in the artery The suture management lumen device 152 may be provided generally central to the needle and suture delivery unit along or within the support 160. The suture management lumen device 152 comprises a plurality of lumens 153, each for receiving a respective suture. Thus, in the embodiment shown, four lumens 153 are provided for receiving four sutures. A slit 154 is associated with each lumen 153. After the needles are deployed and when the sutures are to be deployed, knotted, and/or locked, as described below, the lumen slits 154 permit the sutures to easily be extracted from the lumens 153. Blood flow passages 155 may be provided for blood-flash back during puncture location. Thus, when the puncture in the artery is located, blood flows back through the blood flow passages 155 to give a visual indication of positioning. Cable passages 156 may be provided for accommodating the tensioning cables, used for actuating the legs from the closed configuration to the open, operational configuration. A central bore 157 may be provided for accommodating the actuating wire (see Figure X) used to actuate the pushers 130 for deploying the needles 150.

Returning to FIGS. 1-8, as previously discussed, the leg 110 of the needle and suture delivery unit 100 serves as a guide for the needle carrier tube 120, the pusher 130, and the needle 140 that may be deployed from the needle carrier tube 120. More specifically, the leg 110 moves the needle carrier tube 120 from the closed configuration shown in FIGS. 2a, 3a, and 4 to the open configuration shown in FIGS. 2b-2d, 3b, 3c, 5, and 6 such that the pusher 130 may expel the needle 140 from the tube. Thus, in the open configuration, the legs 110 form a temporary anchoring and firing base for the needles 140 provided in the needle carrier tubes 120. A plurality of legs 110 may be provided. In the embodiments of the figures, four legs 110 are provided. The leg 110 may be constructed of stainless steel, a polymer, or any material suitable for medical devices. The leg 110 may be coupled at one end to the support 160 and one or more tensioning cables 115, and optionally may be coupled at another end to a needle carrier tube 120. The leg 110 may further comprise a passage or aperture through a central region and may be used as a guide or support for other portions of the needle and suture delivery unit 100. The leg 110 is movable from a closed position, shown in FIGS. 2a, 3a, and 4, which is parallel to the support 160, to an open position, shown in FIGS. 2b-2d, 3b, 3c, 5, and 6, in which the leg 110 is disposed at an angle relative the support 160. That angle may range from approximately 30° to approximately 70° or from approximately 30° to approximately 90°.

Figure 10:
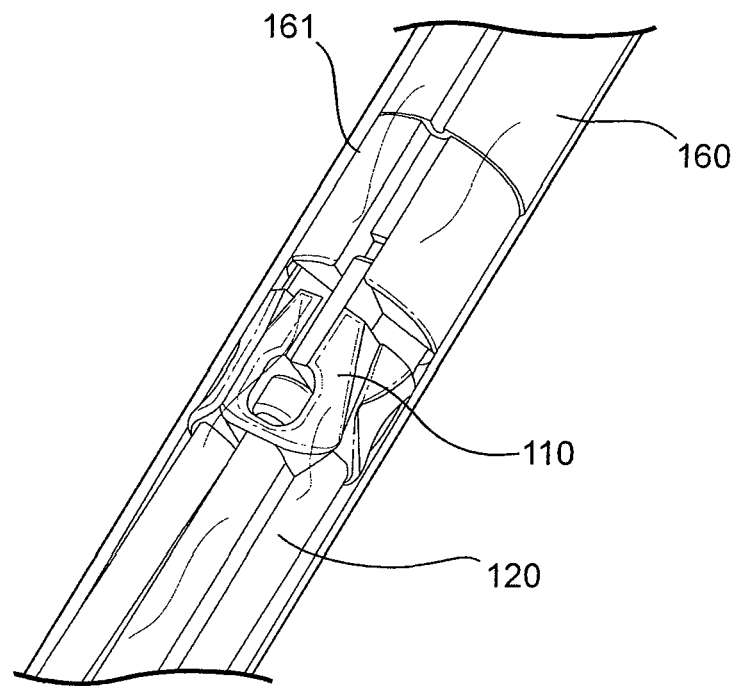
FIG. 10 illustrates legs of a needle and suture delivery unit of the vascular closure delivery system, the needle and suture delivery unit being in a closed configuration, in accordance with one embodiment.
Figure 11:
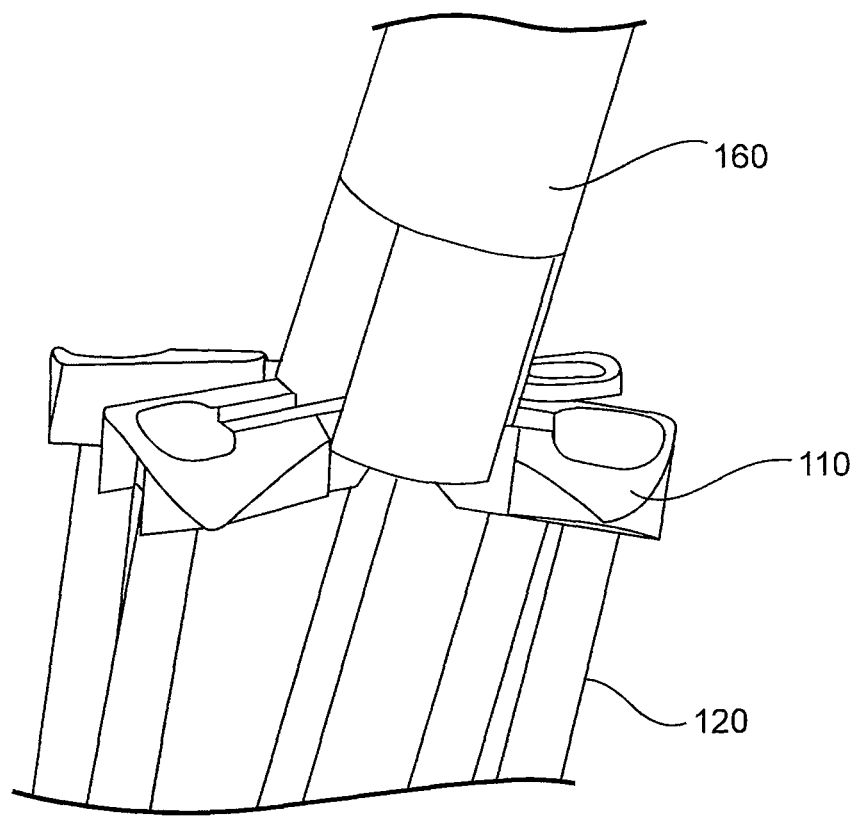
FIG. 11 illustrates legs of a needle and suture delivery unit of the vascular closure delivery system, the needle and suture delivery unit being in a open configuration in accordance with one embodiment.

FIGS. 10 and 11 closely illustrate the relative positioning of the leg 110, support 160, and needle carrier tube 120 in accordance with one embodiment. In the closed position, shown in FIG. 10, the needle delivery tube 120 may generally abut the first end of the leg 110, and be hinged to that end of the leg 110. FIG. 10 further illustrates a covering sheath 161 over the legs 110, needle carrier tubes 120, and support 160 to provide smooth profile for insertion of the needle and suture delivery unit into the wound. In alternative embodiments, in the closed position, the needle carrier tube 120 may overlap a portion of the leg 110. Thus, a portion of the needle carrier tube 120 may lie within the leg 110. Generally, the needle carrier tube 120 and the leg 110 lie parallel to the support 160 and do not protrude beyond the surface of the support 160. As discussed, in the closed position, the needle and suture delivery unit 100 is configured to be insertable into the tissue of the patient, for example into the intima of an artery, and may be enclosed by a sheath so as to avoid subjecting the tissue to unnecessary trauma.

In the open position, shown in FIG. 11, the needle carrier tube 120 pivots about the leg 110, for example via a hinge connection of the needle carrier tube 120 to the leg 110, such that the leg is disposed at an angle to the support 160. In alternative embodiments, in the open position, the leg 110 is at an angle between parallel and perpendicular to the support 160, such as between approximately 30° and approximately 70°. In the open position, the leg 110 moves the needle expulsion end of the needle carrier tube 120 from the support 160, the needle carrier tube 120 pivoting at its coupling to the leg 110 such that it is disposed at an angle to the leg 110. For example, in one embodiment, in the open position, the needle carrier tube 120 is approximately perpendicular to the leg 110. In the open position, the leg 110 serves as a brace for the needle carrier tube 120, but may also be pliable and adaptable to the contours of the vessel. As shown, in the open configuration, the legs form a temporary anchoring and firing base for the needles 140 provided in the needle carrier tubes 120. Thus, when the leg 110 is in the open position, the pusher 130 and needle 140 are positioned for deployment.

Returning to FIGS. 4, 5, and 6, a tensioning cable 115 may be provided coupled to each leg 110 and extending towards the handle 200 or other control mechanism of the delivery device. A single tensioning cable 115 may be provided for coupling to one or more legs 110 or a tensioning cable 115 may be provided for each leg 110. At or near the handle 400 of the vascular closure delivery system, the tensioning cable 115 terminates to a tensioning device such as a spring. In alternative embodiments, a tensioning device provided between the leg 110 and handle 400 may comprise a wire cable having elastic properties or other suitable material that is configured to stretch when under tension. Regardless of the type of tensioning mechanism used, whether a tensioning cable 115 or other tensioning device, the tensioning mechanism serves to actuate the legs 110 from a closed position to an open position, or vice versa. When the leg 110 is in a closed position, the tensioning mechanism is relaxed. When the leg 110 is in an open position, the tensioning mechanism is in tension. The tension exerted on the leg 110 allows it to open to at or near its maximum position, and to flex when contacting a less elastic, nonconforming surface. The tension exerted on the leg 110 slaves the leg 110 in a manner that causes the leg 110 to be pliable so that it moves when contacting more rigid surfaces having a higher tension than the tension exerted on the leg 110. This may allow the needle and suture delivery unit 100, and more specifically, the legs 110 of the needle and suture delivery unit 100, to conform to the interior of the vessel or lumen of interest.

When the leg 110 is in an open position, the needle carrier tube 120 pivots with respect to the leg 110 such that the needle carrier tube 120 is disposed at an angle to the leg 110. In one embodiment, in an open position, the needle carrier tube 120 may be approximately perpendicular to the leg 110. In some embodiments, the needle carrier tube 120 may be coupled to the leg 110 by a male/female connection; in other embodiments, the needle carrier tube 120 may rest inside an opening 111 (see FIG. 5) which extends through an interior region of leg 110, or the needle carrier tube 120 can pass through the opening 111 and extend slightly beyond leg 110 (see FIG. 6). The opening 111 enables the pusher 130 and needle 140 to be slidably disposed in the needle carrier tube 120 to be guided through the leg 110 when in an open position. FIG. 6 depicts the needle and suture delivery unit 100 with the needle engagement end of the pusher 130 extending through and beyond the leg 110. In this embodiment, a needle 140 present in tube 120 before deployment of the pusher 130 is delivered out of needle and suture delivery unit 100 and into tissue as the needle engagement end of pusher 130 reaches its extended position.

FIGS. 5 and 6 illustrate alternative manners of coupling the leg 110 to the needle and suture delivery unit 100. In the illustrations of FIGS. 5 and 6, the leg 110 is in an open position. Thus, the cable 115 is in a state of tension and the leg 110 is capable of pivoting and flexing about its connection point(s), thus providing leg 110 with a flexibility that allows the needle and suture delivery unit and needle delivery unit to conform to the intima of the vessel, artery, or vein of interest thereby minimizing intima trauma. In the embodiment shown, the needle engagement end of the needle carrier tube 120 is the proximal end of the needle carrier tube 120. Thus, the connection point of the cable 115 to the leg 100 is at the proximal end of the needle carrier tube 120 (FIG. 5) and/or the distal end of support 160 proximate the needle expulsion end of the needle carrier tube 120 (FIGS. 5 and 6) When the leg 110 is connected only to the support 160 (FIG. 6), increased flexibility may be provided because it pivots about a single pivot point. Further, flexibility may alternatively be provided by coupling the needle carrier tube 120 to the leg 110 via the opening 111 in a variety of positions (e.g., FIG. 5), rather than via a connection point (FIG. 6).

Figure 12:
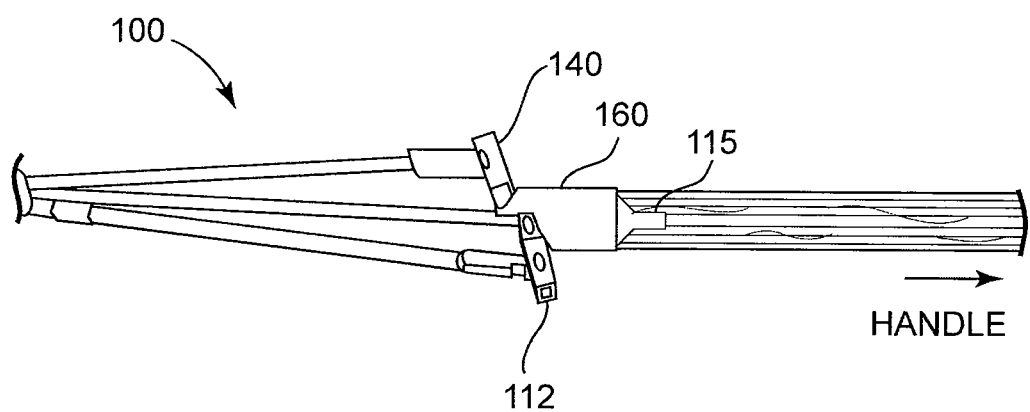
FIG. 12 illustrates a needle and suture delivery unit of the vascular closure delivery system, the needle and suture delivery unit being in an open configuration in accordance with one embodiment.

FIG. 12 illustrates a further embodiment of the needle and suture delivery unit 100 having front legs 110 and back legs 112. The front legs 110 are positioned and angled closer to the distal end of the needle delivery unit, and the back legs 112 are positioned and angled closer to the proximal end of the needle delivery unit and handle 200 or control mechanism. Both the front legs 110 and the back legs 112 may be substantially configured and operated as discussed with respect to the legs 110 of FIGS. 4-6. In the open position, the front legs 110 and the back legs 112 are disposed at angles to the support 160. In one embodiment, the front legs 110 are disposed approximately 70° from the support 160 and the back legs 110 are disposed approximately 30° from the support 160. The front legs and the back legs 110, 112 may be of the same configuration or may be of differing configurations. In the example of FIG. 12, the configurations of the front legs and the back legs 110, 112 are substantially the same with the positioning of the front legs and the back legs 110, 112 on the support 160 resulting in their categorization as front and back.

Each leg 110, 112 is operatively coupled to a tensioning mechanism such as a cable or wire rope extending to the handle; a first cable may be operatively coupled to the front leg(s) 110, and a second cable may be operatively coupled to the back leg(s) 112. Alternatively, a cable may be provided for each leg or all of the legs 110, 112 may be coupled to a single cable. Both the first and second cables may be substantially configured and operated as discussed with respect to the tensioning cable 115 of FIGS. 4-6. In some embodiments, the flexibility of the cables may vary one to the other. For example, a more flexible cable may be coupled to the back leg 112 so that when back leg 112 is suspended in the open position, it has more flexibility compared to front leg 110 coupled to a less flexible cable. The flexibility of legs 110, 112 may also be varied by adjusting spring forces when the first and second cables are coupled to springs.

Figure 13:
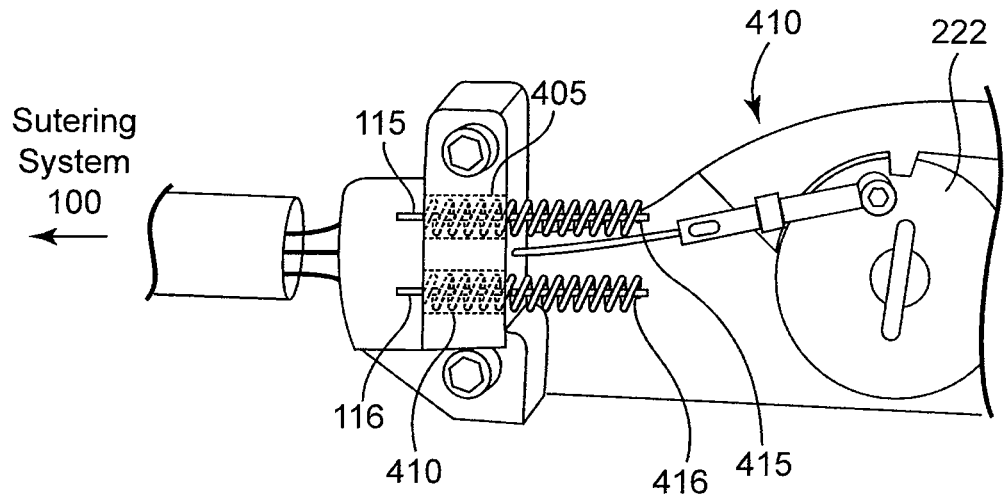
FIG. 13 illustrate a control unit for opening legs of the needle and suture delivery unit of the vascular closure delivery system in accordance with one embodiment.
Figure 14:
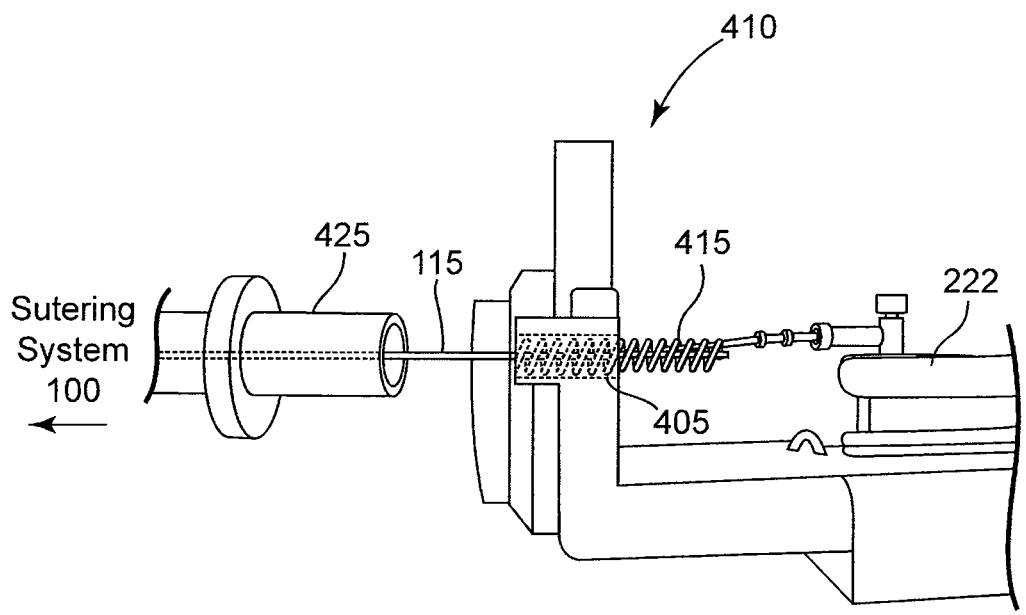
FIG. 14 illustrate a control unit for opening legs of the needle and suture delivery unit of the vascular closure delivery system in accordance with one embodiment.

FIGS. 13 and 14 show a control unit 410 for controlling operations of needle and suture delivery unit 100. The control unit 410 may be located at, on, in, or proximal to the handle 400 of the needle and suture delivery unit. In the embodiments of FIGS. 13 and 14, the control unit 410 is provided as a component of the handle 400. FIG. 13 illustrates a top view of the control unit 410 and springs 415 and 416 coupled to the tensioning cables 115 of FIG. 12. Each of the springs 415 extend both exterior to and through channels 405, 410. In alternative embodiments, springs or other mechanisms and associated channels may have a variety of configurations. Spring forces of springs 415, 416 can be adjusted so that the degree of flexibility of the legs 110, 112 may be controlled or adjusted. Leg flexibility can also be controlled by varying the length of spring channels 405, 410 that house at least a portion of springs 415, 416. Further, the front legs and the back legs 110, 112, described with respect to FIG. 12, may further be configured to have a differing amount of flexibility depending on application. For example, a weaker spring can be used for the back legs to get more flexibility compared to the front legs. In addition, multiple springs, rather than a single spring may be used to control the flexibility of each leg. The above-described features may also be provided by using highly elastic cables that stretch when under tension or using other mechanisms.

FIG. 14 illustrates a side view of the control unit 410 having a tensioning device composed of cables and springs. The tensioning cable 115 is shown extending from the spring 415, through the channel 405, and into sheath 425 where it couples with a leg 110 of the needle and suture delivery unit 100. In the embodiments shown, the needle carrier tube 120 is oriented for expulsion of the needle 140 proximally. Thus, the leg 110 may be moved to the opened configuration by exerting a pull force on the leg 110 and drawing the end of the leg 110 coupled to the needle carrier tube 120 proximally. Thus, a lever or sliding platform, such as actuator 113 of FIGS. 2a-2d, may be provided for exerting a pull force on the leg 110. The tensioning cable(s) 115 may be coupled directly or indirectly to the lever or sliding platform. Once the legs 110, 112 open, the cables 115, 116 are in a state of tension, and the legs 110, 112 are able to pivot about their connection points. Because the tensioning device, including the tensioning cables 115, 116, is operatively coupled to legs 110, 112 via coupling of the cables 115, 116 to the legs 110, 112, respectively, the legs 110, 112 are pliable when subjected to other forces. This increases the overall flexibility of the delivery unit resulting in a delivery unit that can yield to vessel walls or other portions of tissue that can be traumatized from insertion of rigid portions of a delivery unit. To return the needle and suture delivery unit to a closed configuration, the lever or sliding platform, such as actuator 113 of FIGS. 2a-2d, is returned to its original position. Thus, the legs 110, 112 are coupled to the springs 415, 416, giving the legs 110, 122 the ability to flex and return from an open configuration to a closed configuration. In one embodiment, to maintain the legs 110, 112 in an open configuration, the platform of the control unit 410 is moved proximally and maintained or locked in a proximal position. As described more fully below, with the legs 110, 112 in the open configuration, the needles may be deployed, for example by motion of the flywheel 222.

Thus, a lever, such as actuator 113 of FIGS. 2a-2d, is operatively associated with the control unit 410 and may be actuated to pull back the tensioning cables 115, 116, thus pulling back the legs 110, 112 into the open configuration. With the legs in the open configuration, the needle and suture delivery unit 100 is ready for deployment of the needles 140. FIGS. 13 and 14 further illustrate a flywheel 222 that may be used to deploy the pusher 130 to expel the needle 140 from the needle carrier tube 140, as discussed more fully below in reference to FIGS. 17 and 18. While FIGS. 13 and 14 are shown with a flywheel 222 control mechanism, other control mechanisms may alternatively be used. Springs 415, 416 extending both exterior to and through channels 405, 410 form a tensioning mechanism allowing the legs to flex. Leg flexibility can also be controlled by varying the length of spring channels 405, 410 that house at least a portion of springs 415, 416. As discussed, a lever or sliding platform may exert a pull force on the legs to open the legs. When the platform is moved, for example proximally, to open the legs, the springs 415, 416 are in tension. The springs 415, 416 maintain the legs in an open position but permit the legs to flex.

Returning to FIGS. 2a-2d and 3a-3c, the pusher 130 is located at the distal end of the needle and suture delivery unit 100 and pointed towards the proximal end of the needle and suture delivery unit 100 such that the pusher 130 pushes the needle 140 proximally for engagement with tissue. In this embodiment, the needle engagement end of the pusher 130 is the proximal end of the pusher. In alternative embodiments, the pusher 130 may be located at the distal end of the needle and suture delivery unit 100 or between the proximal end and distal end of the needle and suture delivery unit 100 with the pusher 130 pointed towards the distal end of the needle and suture delivery unit 100 such that the pusher pushes the needle distally for engagement with tissue. In this embodiment, the needle engagement end of the pusher 130 is the distal end of the pusher 130. Similarly, the expulsion end of the needle carrier tube 120 may be the proximal end of the needle carrier tube 120 or the distal end of the needle carrier tube 120. In the embodiment of FIGS. 2a-2d and 3a-3c, the expulsion end of the needle carrier tube 120 is the proximal end.

When a needle 140 is provided at the needle engagement end of the pusher 130, the pusher 130 expels the needle 140 from the needle carrier tube 120 as the needle engagement end of the pusher 130 moves towards an exit point or expulsion end of the needle carrier tube 120. After expulsion of the needle 140, the pusher 130 may be retracted back into the needle carrier tube 120.

The pusher 130 may be configured to push the needle 140 from the needle carrier tube 120, for example by contacting the opposite end of the needle 140 with the needle engagement end of the pusher 130 and pushing it out of the needle carrier tube 120. Alternatively, as shown in FIG. 6, the pusher 130 may be configured for carrying the needle 140 out of the needle carrier tube 120. In this embodiment, the cross section of the pusher 130 complements the cross section of the needle 140 and is smaller than the cross section of the needle 140.

Further, the opposite end of the needle 140 is at least partially hollow such that it may receive the needle engagement end of the pusher 130. Thus, the needle 140 receives the needle engagement end of pusher 130 at the opposite end of the needle 140. The pusher 130 then may be moved to project from the needle carrier tube 120 and thus carry the needle 140 from the needle carrier tube 120.

Thus, the pusher 130 and needle 140 may be slidably disposed within the needle carrier tube 120 such that the pusher 130 moves therein to expel the needle 140 therefrom, either by pushing the needle 140 from the needle carrier tube 120, by carrying the needle 140 out of the needle carrier tube 120, or other. The needle carrier tube 120 may have any suitable cross section for slidably receiving the pusher 130 and the needle 140. For example, the needle carrier tube 120 may have a circular cross section or a square cross section. In the embodiments shown, the needle carrier tube 120 has a circular cross section. The needle carrier tube 120 may have a slot to allow loading of a needle 140 having a suture 150 coupled thereto between the sharp end of the needle and the opposite end of the needle. Thus, a slot may be provided for allowing the suture to slide freely during loading or deployment. In alternative embodiments, for example, where the suture 150 is coupled to the needle 140 at the opposite end thereof, no slot may be provided in the needle carrier tube. The needle 140 within the needle carrier tube 120 may be provided at a needle engagement end of the pusher 130. The needle 140 may be oriented in the needle carrier tube 120 for expulsion sharp-end first or sharp-end last.

Movement of the pusher 130 towards the needle expulsion end of the needle carrier tube 120 is triggered by an actuator 112 of the handle 400. The actuator 112 may be provided with, in, on, or proximate the handle 400. As described with reference to FIGS. 2a-2d, a further actuator 230 may be provided for returning actuating members 240 (see FIG. 6) to their closed or predeployment configuration. FIGS. 15-18 illustrate the interior of the handle 400 in accordance with various embodiments. The actuator 112 (see FIGS. 2a-2d and 3a-3c) uses a triggered force to automatically deploy the needle 140 via movement of the pusher 130, for example with the push of a button. Such triggered force may be a spring force, a pneumatic force, a magnetic force, or other force. For the purposes of illustration, a spring force is herein described.

As shown in FIGS. 15-18, the actuator 112 is associated with a spring 210 and a control 220 The spring 210 is pulled to store energy. Thus, the control 220 keeps the spring 210 in tension until actuation is desired. The control 220 is coupled directly or indirectly to actuating member(s) 240 (See FIG. 6). The actuating member(s) 240 is coupled to the pusher(s) 130. Such coupling may be done in any suitable manner. In one embodiment, the actuating member(s) 240 is crimped to the pusher(s) 130. As shown in FIG. 6, a single actuating member 240 may be operatively associated with a plurality of pushers 130, for example four pushers. The control 220 is released to cause automated deployment of the needle 140. Such automated deployment is via the actuating members 240 acting on the pusher 130 and the pusher 130 acting on the spring 210. In some embodiments, the control 220 may act on the pusher 130 without an intermediate actuating member. Regardless of whether an actuating member 240 is provided, the pusher 130 is compelled to move towards the expulsion end of the needle carrier tube 120 by release of the spring 210, thus deploying the needle 140 from the needle carrier tube 120. The direction of movement of the pusher 130 may be varied to suit the orientation of the needle and suture delivery unit 100. Thus, when it is desired to deploy the needles proximally from a distal position, as shown in FIGS. 2a-2d and 3a-3c, the pushers 130 move proximally. This may be done, for example, by exerting a pull force on the pushers 130. Conversely, when it is desired to deploy the needles distally from a proximal position, the pushers move distally. This may be done, for example, by exerting a push force on the pushers 130. Depending on the type of control 220 used, described below, the pusher 130 (and actuating member 240 if provided) may automatically be retracted or may be manually retracted.

Figure 15:
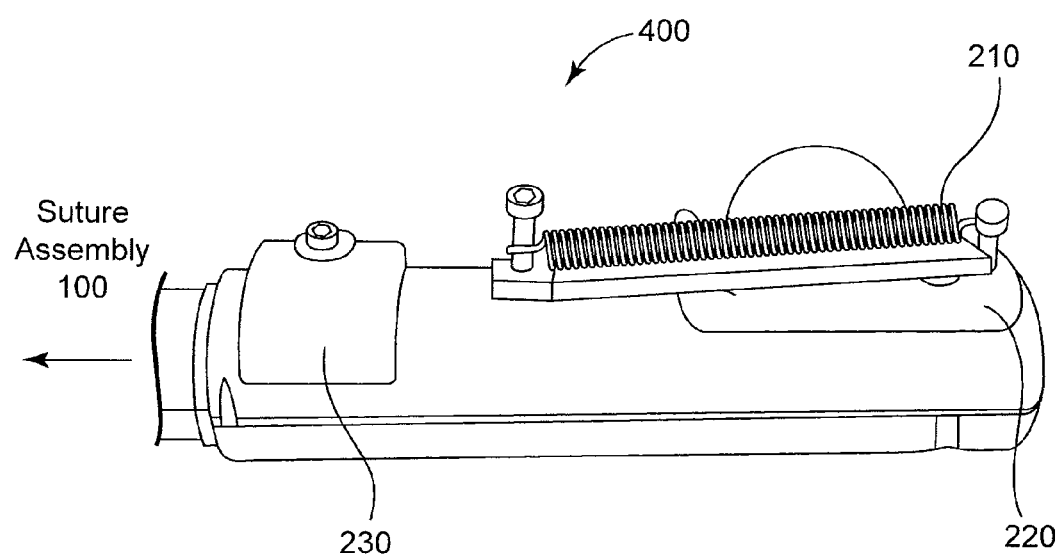
FIG. 15 illustrates an actuator for deploying needles of the needle and suture delivery unit of the vascular closure delivery system, the actuator having a compression spring and the compression spring being in an extended configuration, in accordance with one embodiment.
Figure 16:
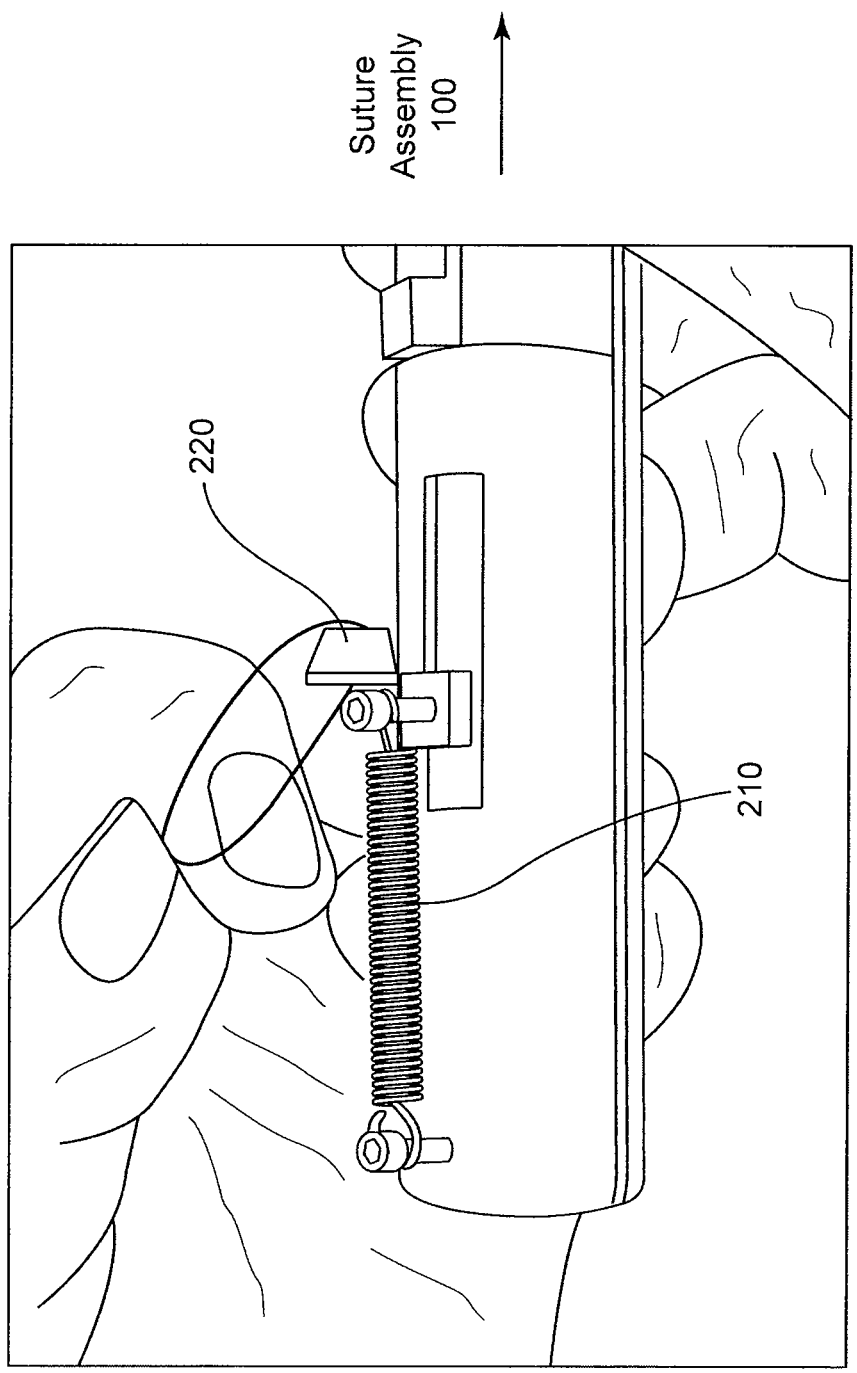
FIG. 16 illustrates the actuator of FIG. 15 with the compression spring in a relaxed configuration.

In one embodiment, shown in FIGS. 15 and 16, the control 220 is a control lever and the spring 210 is a compression spring. As shown in FIG. 15, the compression spring 210 is kept in tension by the lever 220. The control lever 220 is released, for example by pulling of the control lever 220, shown in FIG. 16, to release the spring 210 and move the pusher 130 or actuating member. If an actuating member 240 is provided, the actuating member 240 in turn acts on the pusher 130. The pusher 130 is thus moved (directly by the spring 210 or via the actuating member 240) towards the expulsion end of the needle carrier tube 120 to deploy the needle 140. In one embodiment, an actuating member 240 comprising a nitinol wire is provided. The actuating member 240 has first and second ends. The first end is coupled to the pusher 130 and the second end is coupled to the compression spring 210. When the control lever 220 is released, the spring moves to a released position that moves the extended end of the spring proximally. The proximal movement of the spring causes the actuating member 240 to move proximally, which in turn causes the pusher 130 to move proximally. The proximal movement of the pusher 130 causes the needle 140 to move proximally towards an expulsion end of the needle carrier tube 120 such that the needle 140 is expelled from the needle carrier tube 120 in the proximal direction. The actuating member 240 may be coupled to the pusher 130 at any suitable location such that a pull force exerted on the actuating member 240 will exert a pull force on the pusher 130. In one embodiment, the actuating member 240 is coupled to the pusher 130 proximate the needle engaging end of the pusher 130. FIG. 16 illustrates the spring 210 in a released state.

The control lever 220 may be released using any suitable mechanism. For example, a push button or release knob, such as the actuator 112 of FIGS. 2a-2d, may be provided to release the control lever 220. In one embodiment, the control lever 220 comprises a rectangular component that maintains the spring 210 in an extended position until release. When the control lever 220 is released, for example using the actuator 112, the spring is released to deploy the needles via the actuating members acting on the pushers. A second mechanism, shown in FIG. 15 as a push button 230, may be provided to retract that actuating members. For example, a further spring may be provided that is actuated upon pushing of the push button 230, actuation of the spring retracting the actuating member 240. Alternatively, a single mechanism may be provided to release the control lever and retract the actuating members. Such release and retraction may be done using separate actuations of the mechanism.

Figure 17:
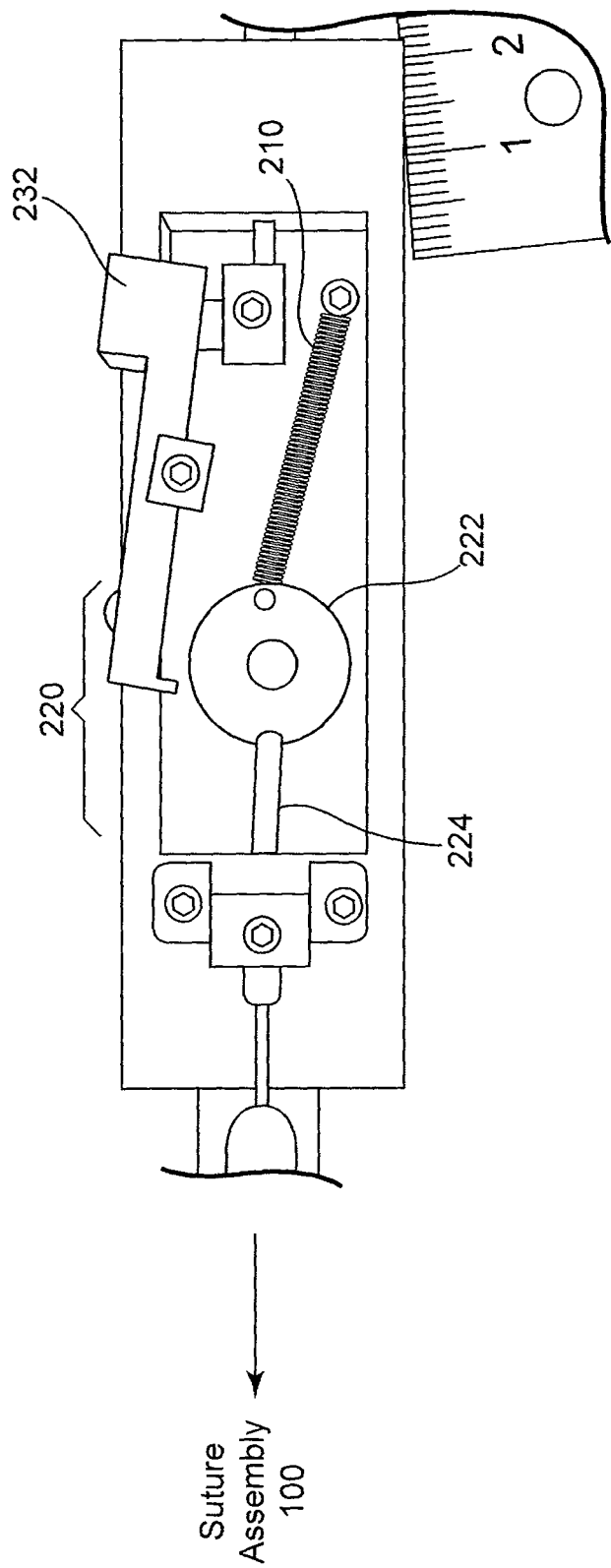
FIG. 17 illustrates an actuator for deploying needles of the needle and suture delivery unit of the vascular closure delivery system, the actuator having a flywheel, in accordance with one embodiment.

FIG. 17 illustrates an alternative embodiment using a flywheel control 220, such as referred to in FIGS. 13 and 14, and a compression spring 210. The flywheel control 220 comprises a flywheel 222 and a center rod 224. The center rod 224 is operatively associated with the pusher 130 or, if provided, actuating member 240. A release button 232 (corresponding to actuator 112 of FIGS. 2a-2d). is provided for releasing the compression spring 210, causing rotation of the flywheel 222. In embodiments using a flywheel control 220, a single actuator may be used to deploy the needles via the actuating member 240 and return the actuating member to the pre-deployment position. Thus, the release button 232 acts in the place of actuators 112 and 230 of FIGS. 2a-2d. Rotation of the flywheel 222 moves the center rod 224 which causes movement of the actuating member 240 and/or pusher 130. In one embodiment, the center rod 224 is coupled to an actuating member 240 such as a nitinol wire. The actuating member 240 thus is coupled at one end to the pusher 130 and at the other end to the center rod 224. When the flywheel control 220 is released, the flywheel 222 rotates, causing movement of the center rod 224 in the proximal direction. The proximal movement of the center rod 224 causes the actuating member 240 to move proximally, which in turn causes the pusher 130 to move proximally. The proximal movement of the pusher 130 causes the needle 140 to move proximally towards an expulsion end of the needle carrier tube 120 such that the needle 140 is expelled from the needle carrier tube 120 in the proximal direction. The actuating member 240 may be coupled to the pusher 130 at any suitable location such that a pull force exerted on the actuating member 240 will exert a pull force on the pusher 130. In one embodiment, the actuating member 240 is coupled to the pusher 130 proximate the needle engaging end of the pusher 130.

With use of a flywheel 222, after movement towards the expulsion end of the needle carrier tube 120, the actuating member 240 and/or pusher 130 automatically retracts into the needle carrier tube 120 as rotation of the flywheel 222 continues. Thus, half of the revolution of the flywheel drives the or actuating member 240 and/or pusher 130 towards the expulsion end of the needle carrier tube 120 and the other half of the revolution of the flywheel 222 retracts the actuating member 240 and/or pusher 130. Thus, a single actuator, release button 232, controls release of the spring and retracting of the actuating member 240 and/or pusher 130.

Figure 18:
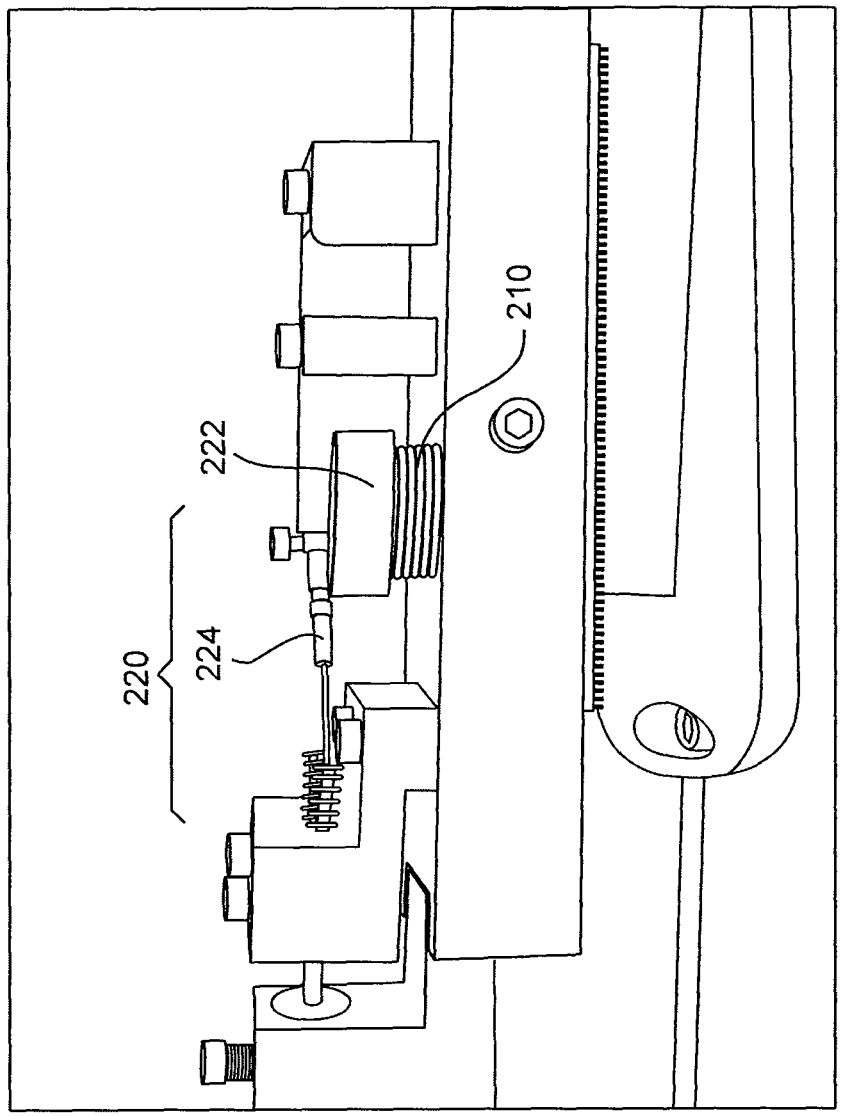
FIG. 18 illustrates an actuator for deploying needles of the needle and suture delivery unit of the vascular closure delivery system, the actuator having a torsion spring in accordance with one embodiment.

An alternative flywheel embodiment is illustrated in FIG. 18 showing a torsion spring. Thus, the control 220 comprises a flywheel 222 and a center rod 224 and the spring 210 comprises a torsion spring. Using a torsion spring, the spring is rotated (rather than pulled) to store energy. A release button 230 is provided for releasing the compression spring 210, causing rotation of the flywheel 222. Rotation of the flywheel 222 in turn moves the center rod 224 which causes movement of the actuating member 240 and/or pusher 130. In one embodiment, the center rod 224 is coupled to an actuating member 240 (see FIG. 6) such as a nitinol wire. The actuating member 240 thus is coupled at one end to the pusher 130 and at the other end to the center rod 224. When the flywheel control 220 is released, the flywheel 222 rotates, causing movement of the center rod 224 in the proximal direction. The proximal movement of the center rod 224 causes the actuating member 240 to move proximally, which in turn causes the pusher 130 to move proximally. The proximal movement of the pusher 130 causes the needle 140 to move proximally towards an expulsion end of the needle carrier tube 120 such that the needle 140 is expelled from the needle carrier tube 120 in the proximal direction. The actuating member 240 may be coupled to the pusher 130 at any suitable location such that a pull force exerted on the actuating member 240 will exert a pull force on the pusher 130. In one embodiment, the actuating member 240 is coupled to the pusher 130 proximate the needle engaging end of the pusher 130.

As described with reference to FIG. 17, with use of a flywheel 222, after movement towards the expulsion end of the needle carrier tube 120, the actuating member 240 and/or pusher 130 automatically retracts into the needle carrier tube 120 as rotation of the flywheel 222 continues. Thus, half of the revolution of the flywheel drives the actuating member 240 and/or pusher 130 towards the expulsion end of the needle carrier tube 120 and the other half of the revolution of the flywheel 222 retracts the actuating member 240 and/or pusher 130. Thus, a single actuator, release button 230, controls release of the spring 210 and retracting of the actuating member 240 and/or pusher 130.

Figure 19:
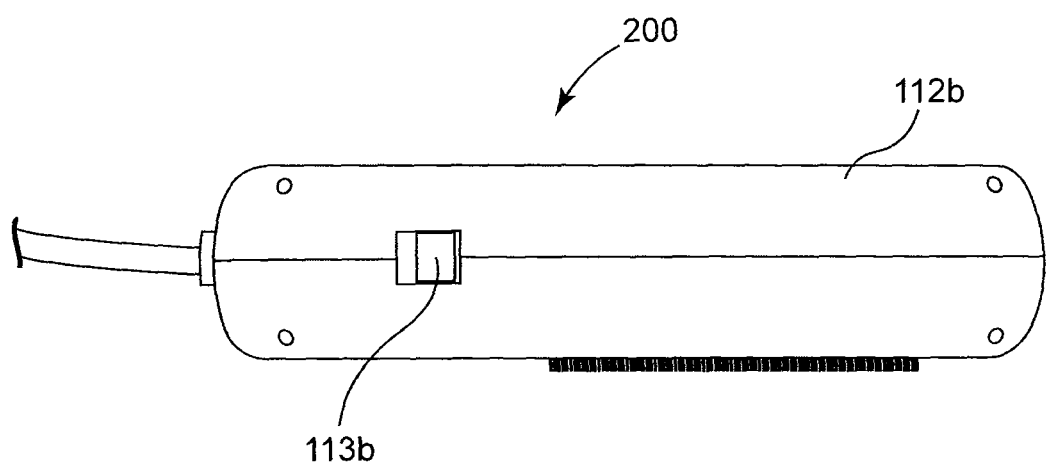
FIG. 19 illustrates a handle of the vascular closure delivery system in accordance with one embodiment.

FIG. 19 illustrates an alternative embodiment of a handle 400 that may be used to open the legs, deploy the needles, and close the legs. As shown, a lever 113b is provided. The lever 113b may be retracted to pull back a sheath provided over the needle and suture deployment unit 100 and actuate the legs 110 via a pull force. A push button 112b is further provided. The push button 112b may be used to deploy the pushers 130 and thus the needles 140. The needles are thereby expelled from the needle carrier tubes 120 and engage tissue. An actuator such as button may be provided to collapse the legs (for example, actuator 230 of FIG. 2d). To open the legs, the actuator 113 is pulled proximally. The actuator 230 acts as a stop to hold the sliding platform in position. While the legs are open, a spring is in tension such that release of the spring closes the legs. Thus, when the actuator 230 is released, and thus removed from the stopping position, the spring pushes the platform distally and closes the legs.

Figure 20:
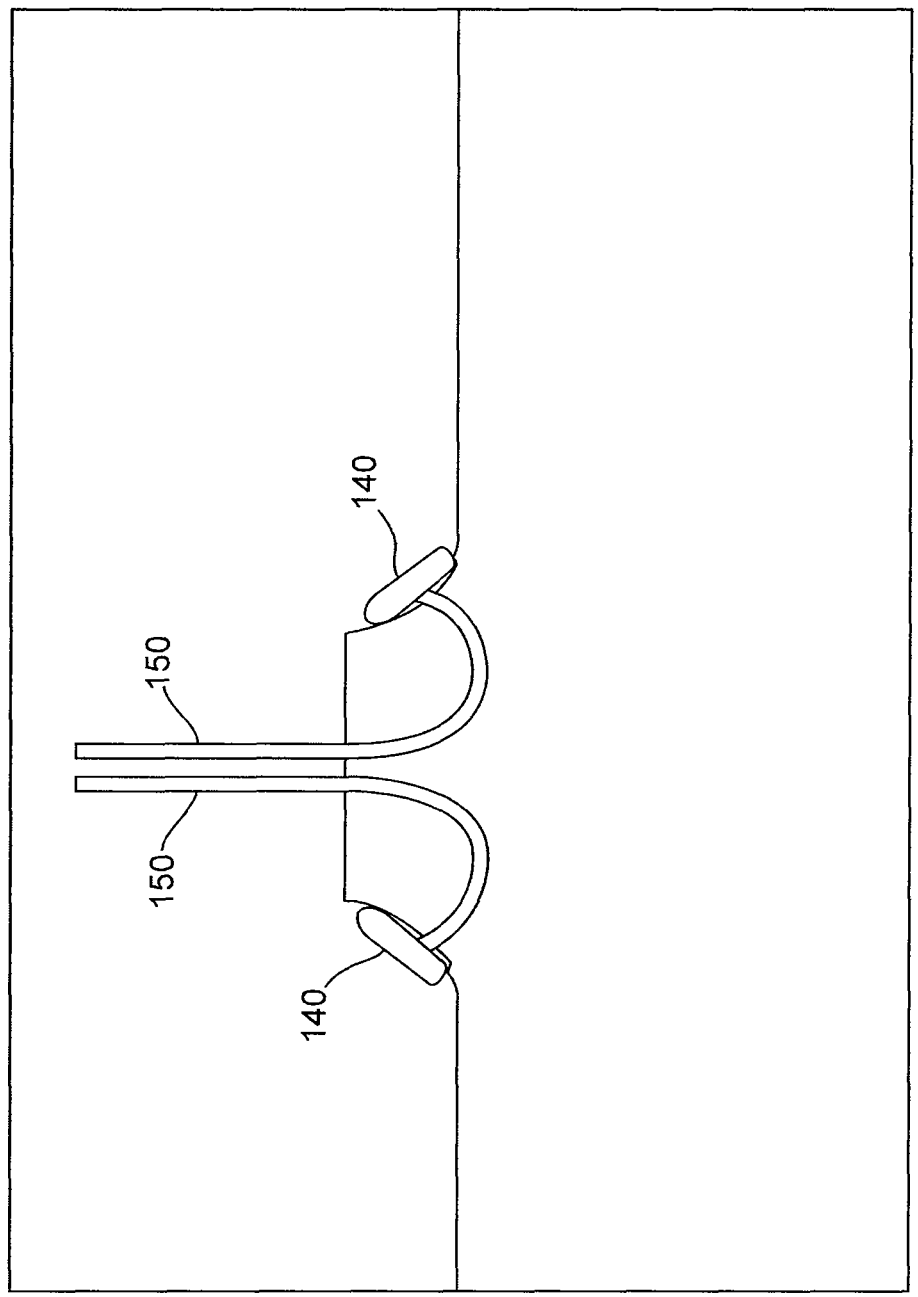
FIG. 20 illustrates an everted wound lip with needles deployed therein and sutures extending therethrough in accordance with one embodiment.

FIG. 20 illustrates a cross sectional view of an everted wound lip 260 having needles 140 and sutures 150 engaged therethrough. FIG. 20 illustrates first and second needles 140. It is to be appreciated that third and fourth needles 140 would be present in a plan perpendicular to the page. In alternative embodiments, more or fewer needles 140 may be provided. As shown, sutures 150 extend back from the needles 140. Thus, after deployment of the needles 140, the sutures 150 may be tied or otherwise set in place.

The suture knot system 300 of the vascular closure delivery device may be used for advancing surgical knots on the suture 150 to tie the suture after the needle 140 has been deployed. Generally, to advance overhand suture loops to a surgical site with percutaneous delivery, it is desirable to separate each suture loop during advancement. By providing two loops, the first loop may approximate the wound lips and seal the hole in the vessel and the second loop may secure the sealing result, tightening the knot, and maintaining tightness of the seal during pulsation. Thus, two overhand suture loops are provided on the suture 150. The suture knot system 300 comprises an suture portion 5, shown in FIGS. 21 and 22, and a handle 310, shown in FIGS. 23 and 24.

Figure 21:
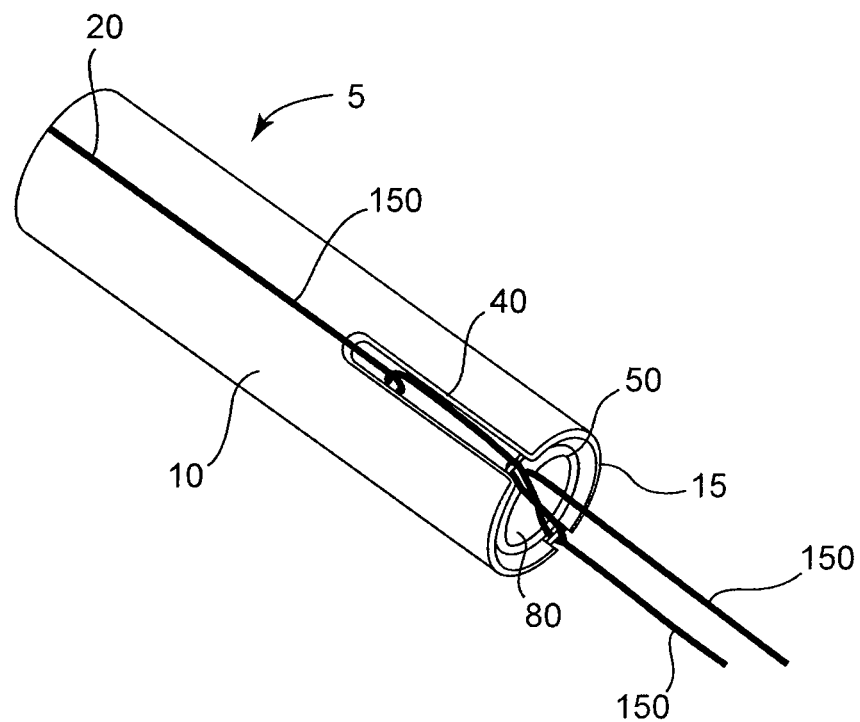
FIG. 21 illustrates a distal end of a suture knot system of the vascular closure delivery system in accordance with one embodiment.
Figure 22:
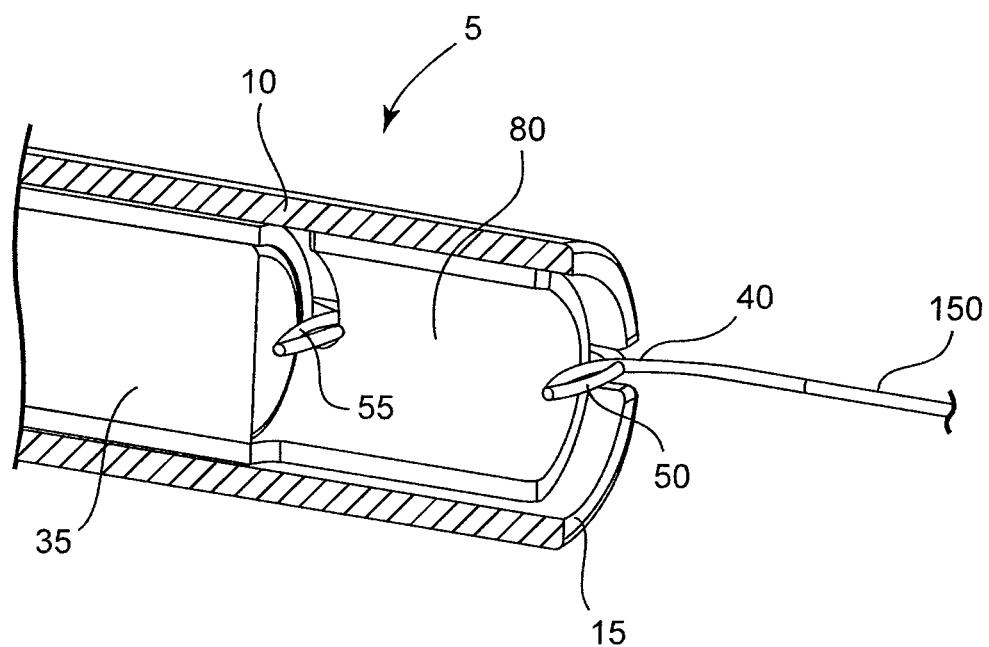
FIG. 22 illustrates a distal end of a suture knot system of the vascular closure delivery system in accordance with one embodiment.
Figure 23:
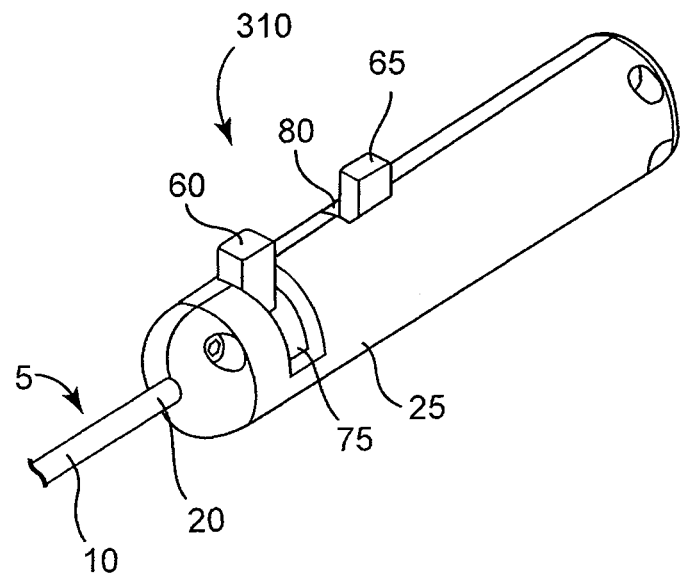
FIG. 23 illustrates an actuator assembly of a suture knot system of the vascular closure delivery system in accordance with one embodiment.

Referring to FIGS. 21 and 22, the suture portion 5 includes an outer shaft 10 having a distal end 15 and a proximal end 20. The sutures 150 are associated with the suture portion 5. The outer shaft 10 includes one or more axial passages 40 extending over at least a portion of the length of the outer shaft 10. As shown, the axial passages 40 begin at the distal end 15 and terminate distally of the proximal end 20. As shown in FIGS. 22 and 23, the proximal end 20 is received by the handle 302.

An inner tubular member 80 is provided within outer shaft 10. The inner tubular member 80 extends substantially from the distal end 15 of the outer shaft 10 to the proximal end 20 of the outer shaft 10. The inner tubular member 80 may be generally concentric with the outer shaft 10. In the embodiment shown, the inner tubular member 80 has a semicircular profile along its entire length. In alternative embodiments, the inner tubular member 80 may have varying profiles. The inner tubular member 80 is radially translatable with respect to the outer shaft 10. As can be best seen in FIG. 21, the distal end of the inner tubular member 80 may be slightly recessed from the distal end 15 of the outer shaft 10.

An inner rod 35, shown in FIG. 22, may be provided with the inner tubular member 80. The inner rod 35 may be formed of any suitable material. Softer materials, such as a polymeric material, generally allow for ease of transport along the suture filaments 52 because a lower dynamic friction is caused by the softer inner rod 35 traveling along the suture filament 52. The inner rod 35 is axially translatable within the inner tubular member 80. The distal end of inner rod 35 is shown in its fully retracted position in FIG. 22.

With particular reference to FIG. 22, the distal end of the outer shaft 10 houses first and second suture knots. The knot pusher device is specifically described with reference to deploying first and second overhand suture loops. However, the knot pusher device may be used for deploying a plurality of any type of suture knots and is generally useful for deploying multiple pre-tied knots. In the embodiments shown, the outer shaft 10 houses a first overhand suture loop 50 and a second overhand suture loop 55. In alternative embodiments, the number of suture knots may be more than or less than two. Sutures 150 extend from the first and second overhand suture loops 50, 52.

Figure 24:
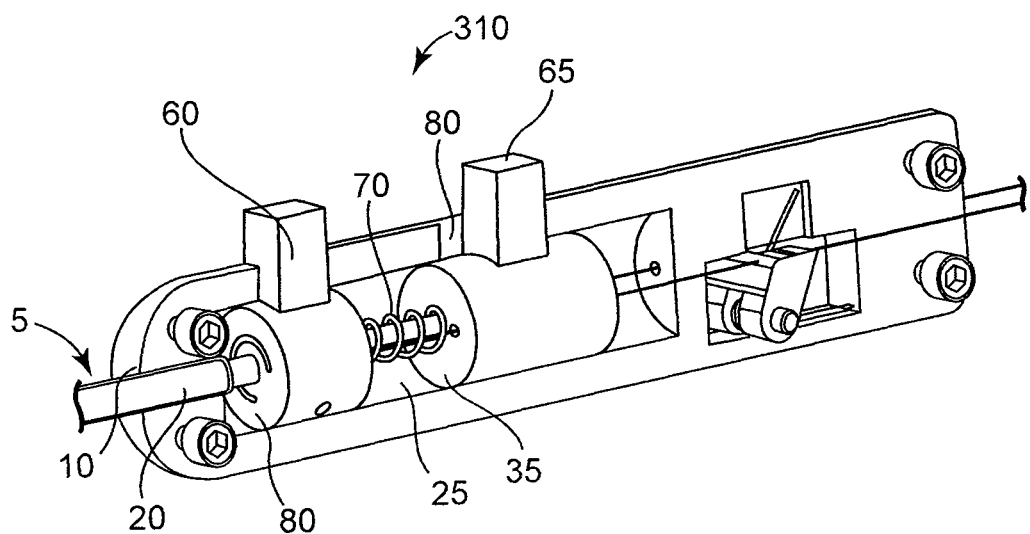
FIG. 24 illustrates an actuator assembly of a suture knot system of the vascular closure delivery system in accordance with one embodiment.

Referring to FIGS. 23 and 24, an actuator assembly 25 is provided with the handle 310. The actuator assembly 25 may be used to affect radial translation of the internal tubular member 80 and axial translation of the inner rod 35 within the outer shaft 10. In the embodiment shown, the actuator assembly 25 is coupled to the proximal end 20 of the outer shaft 10. The actuator assembly 25 may be configured in any manner suitable for affecting radial translation of the internal tubular member 80 and axial translation of the inner rod 35 to move the first and second overhand suture loops 50, 55 as described below. In the embodiment shown, the actuator assembly 25 comprises a first actuator knob 60 and a second actuator knob 65. The first actuator knob 60 is operatively associated with the inner tubular member 80 of the suture portion 5. The second actuator knob 65 is operatively associated with the inner rod 35 of the suture portion 5 and a compression spring 70. As shown in FIG. 24, the distal end of the inner rod 35 extends through the compression spring 70.

The inner tubular member 80 can be rotated or radially translated by displacing the first actuator knob 60 radially through a first actuator slot 75. In one embodiment, the inner tubular member 80 can be rotated up to approximately 90 degrees. Prior to rotation, or with the first actuator knob 60 in the position shown in FIG. 23, the inner tubular member 80 is considered in the closed configuration. FIG. 22 illustrates the inner tubular member 80 in the closed position. In the closed position, the inner tubular member 80 prevents axial translation of the second overhand suture loop through the axial passages 40. After rotation, or with the first actuator knob 60 rotated approximately 90 degrees in the first actuator slot, the inner tubular member 80 is considered in the open configuration, described more fully below.

The spring 70 is maintained under compression between the first actuator knob 60 and the second actuator knob 65 such that the second actuator knob 65 remains proximally retracted relative to the inner rod 35. The inner rod 35 may be driven distally, or axially translated, by displacing the second actuator knob 65 axially through a second actuator slot 80. It will be appreciated that a wide variety of other actuator mechanisms could alternatively be used.

Referring again to FIG. 22, the first overhand suture loop 50 and the second overhand suture loop 55 are pre-tied and arranged in the suture portion 5. As a pushing force is applied to the suture portion 5, for example, by manually pushing the suture knot device, including the handle 310 and the suture portion 5, the knots 50, 55 are driven distally toward a surgical site, until the distal end of the suture portion 5 contacts the surgical site, or until force is no longer applied.

When the suture portion 5 contacts the surgical site, the first suture loop 50 may be deployed at the surgical site. In embodiments where the first suture loop 50 is a pre-tied knot, the first suture loop 50 is substantially deployed upon contacting the surgical site. To provide a tight and secure knot over the site, forward pressure may be applied to the handle 100 while a tensioning action is applied to the tensioning knob 312. Generally, more pressure applied to the handle 100 and tensioning knob 312 creates more security in the knot. The first suture loop 50 approximates the wound lips and seals the surgical site. Thus, when used to seal an arteriotomy, the first suture loop 50 affects closure of the arteriotomy.

Upon contact of the suture portion 5 with the surgical site, the second overhand suture loop 55 may also be deployed at the surgical site. In one embodiment, deployment of the second overhand suture loop 55 is accomplished by first displacing the first actuator knob 60 radially through the first actuator slot 75. Such actuation causes the inner tubular member 80 to rotate from the closed position to the open position. In the open position, the inner tubular member 80 is aligned with the axial passage 40 such that the second overhand suture loop 55 is free to advance in the distal direction.

The second overhand suture loop 55 is driven in the distal direction by actuation of the second actuator knob 65 axially through the second actuator slot 80. Such actuation causes the inner rod 35 to be driven distally, which, in turn, drives the second overhand suture loop 55 distally through axial passages 40 and out of the suture portion 5 through the lumen 85. The second suture loop 55 secures the sealing result of the first suture loop 50, tightens the knot, and minimizes any loosening of the knot under pulsation.

During deployment of the knots 50, 55 to the surgical site, it may be desirable to keep the sutures 150 in tension. More specifically, it may be desirable to keep the sutures 150 at the end of the handle 310 in tension. This can be done by pulling the sutures 150 proximally, manually or by using a tensioning knob 312, while advancing the handle 310 to deliver the knots 50, 55. FIG. 34 illustrates a vascular closure delivery system including the suture knot system 300. As shown, a tensioning knob 312 may be disposed at a proximal end of the handle 310. A suture lock device 400, described with reference to FIGS. 25-33, may be provided at the distal end of the suture portion 5. Sutures 150 extend from the surgical site, through the suture portion 5 and, optionally, through the handle 310 to the tensioning knob 312. The sutures 150 travel through the handle 310 and the handle 310 can be used as a pusher to push the suture knots 50, 55 of FIGS. 21 and 22. This arrangement keeps the sutures 150 substantially in tension while the suture knots 50, 55 and, optionally, the suture lock device 400, are being deployed. The tensioning knob 312 may additionally be pulled or actuated to affirmatively tense the sutures. By keeping the sutures substantially in tension during knot deployment, slack in the sutures between the suture site and the knots as deployed is substantially avoided.

As previously discussed, the needle and suture delivery unit 100 deploys the needles 140 through the everted wound lip. The sutures 150 extend from the needles 140 to the suture knot system 300. After deployment of the needles 140, the needle and suture delivery unit 100 may be removed and the suture knot system 300 kept in place. Thus, while FIG. 1 illustrates the suture knot system 300 coupled to the needle and suture delivery unit 100, such coupling is not permanent. After deployment of the needles 140, the sutures 150 extend proximally and enter the distal tip of the suture portion 5 of the suture knot system 300. Thus, after removal of the suture and needle delivery unit 100, the sutures 150 extend from the surgical site back to the suture knot system 300, where they are arranged in a pre-tied fashion. The physician can then either close the would immediately or perform other procedures before closing the wound. Such techniques may be referred to as pre-close techniques wherein the sutures are in place before the wound is dilated to its final size. Thus, the risk of bleeding may be reduced and the wound can be closed simultaneously with retraction of an interventional sheath.

A suture lock 400 or suture attachment device, shown in FIGS. 25-33, may be provided with the suture knot system 300 for locking the sutures 150 in place after the sutures have been tied. The suture attachment device 400 may be used for fastening multiple sutures 150 at the wound or surgical site.

Figure 25:
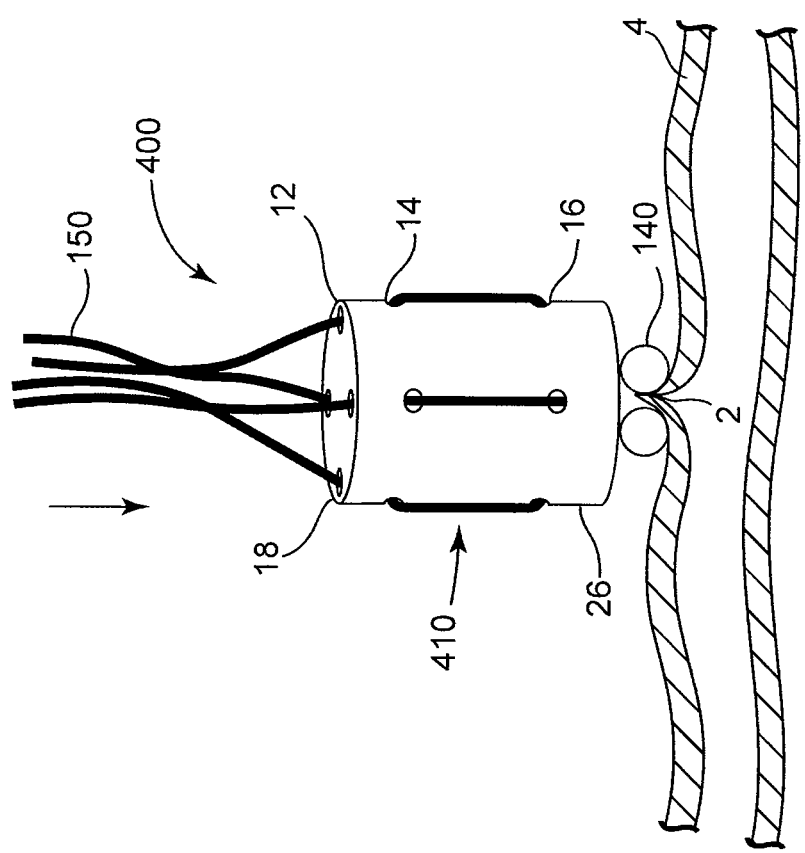
FIG. 25 illustrates a lock body of a suture attachment device deployed at a vascular puncture in accordance with one embodiment.
Figure 26:
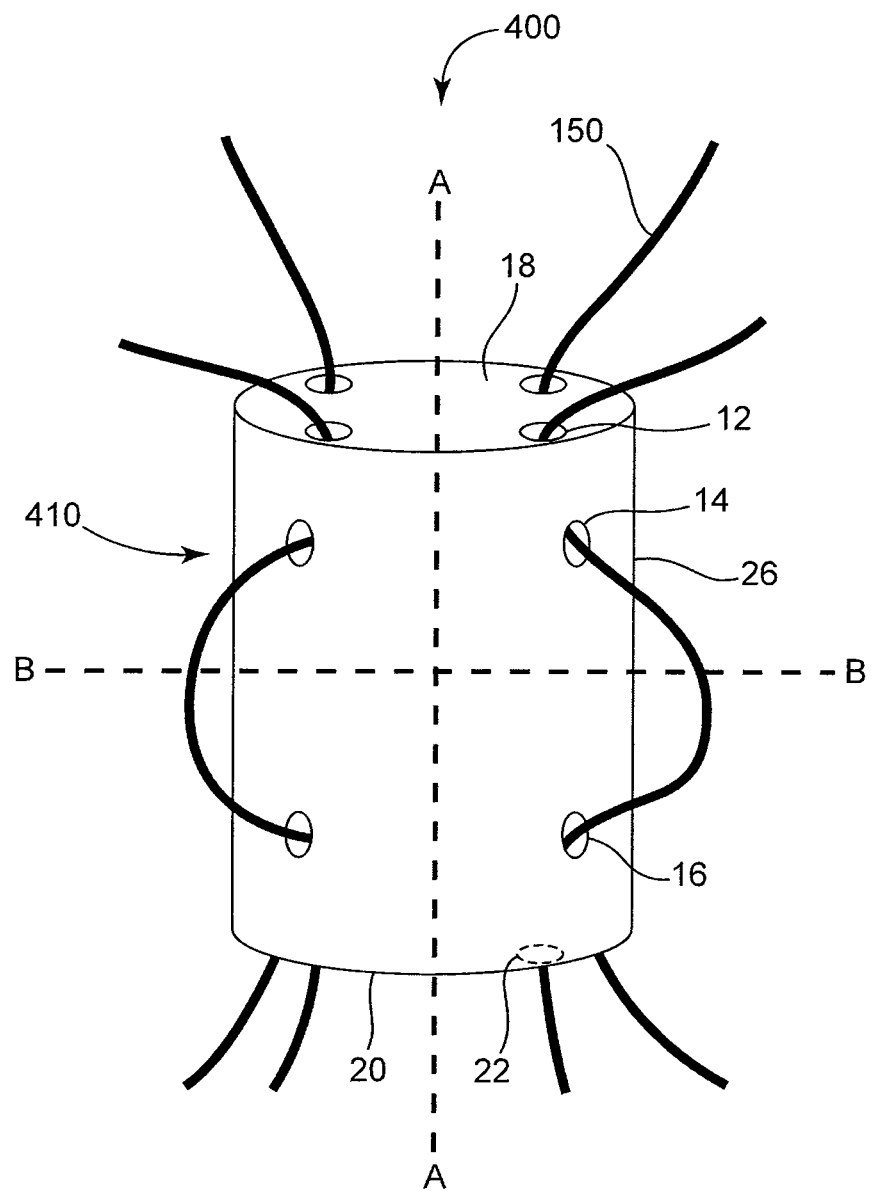
FIG. 26 illustrates a lock body of a suture attachment device in accordance with one embodiment.
Figure 27:
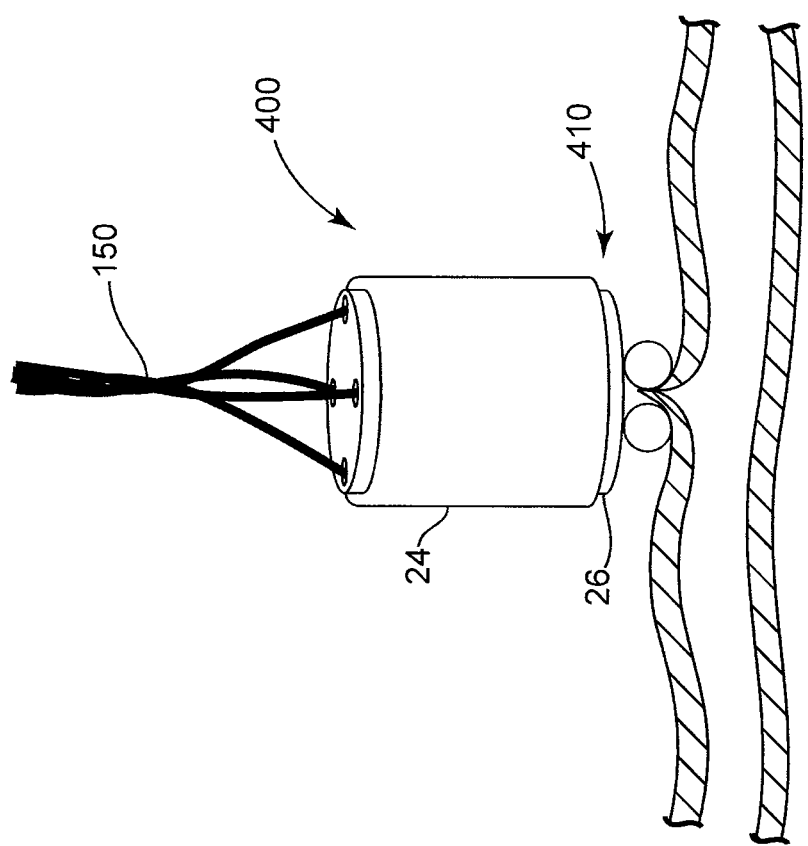
FIG. 27 illustrates an outer sleeve of a suture attachment device deployed over a lock body of a suture attachment device deployed at a vascular puncture in accordance with one embodiment.

A first embodiment of the suture attachment device 400 is shown in FIGS. 25-27. As shown, the suture attachment device 400 (or suture lock) includes a lock body 410 and, optionally, an outer sleeve 24. Either or both of the lock body 410 and the outer sleeve 24 may be manufactured as a machined or molded bioabsorbable material such as an implant grade polymer. Alternatively, the lock body 410 and the outer sleeve 24 may be any suitable material manufactured in any suitable manner. In one embodiment, the lock body 10 is manufactured of an elastic material such that the lock body 10 has a flexible or nonrigid characteristic. Generally, the lock body 10 is manufactured of an elastic material such that the lock body 10 has a flexible or nonrigid characteristic. In one embodiment, the lock body 10 and the outer sleeve 24 are flexible such that they conform around the sutures to wrap the sutures. In some embodiments, the sleeve 24 is more flexible than the lock body 10. The lock body 410 and the outer sleeve 24 may have complementary shapes such that the lock body 410 receive the outer sleeve 24 there around, as is described more fully below. It should be noted that it is not necessary that the lock body 410 and the outer sleeve 24 have identical shapes. In the embodiment shown, both the lock body 410 and the outer sleeve 24 are substantially cylindrical. Alternatively, either or both of the lock body 410 and the outer sleeve 24 may be rectangular, spherical, or otherwise shaped. The lock body 410 extends along a longitudinal axis (axis line B-B of FIG. 26), substantially perpendicular to a radial axis (axis line A-A of FIG. 26).

With particular reference to FIG. 26, the lock body 410 includes a proximal surface 18 (farthest away from the vascular puncture) and a distal surface 20 (closest to the vascular puncture). One or more proximal surface passageways 12 are provided on the proximal surface 18. One or more distal surface passageways 22 are provided on the distal surface 20. In the embodiment shown, the lock body 410 includes four proximal surface passageways 12 and four distal surface passageways 22. In alternative embodiments, more or fewer proximal surface passageways 12 or distal surface passageways 22 may be provided. In the embodiment shown, an equal number of proximal surface passageways 12 is provided as distal surface passageways 22. In alternative embodiments, the number of proximal surface passageways 12 and the number of distal surface passageways 22 may not be equal.

One or more proximal apertures 14 are provided on an external wall 26 of the lock body 410. Each proximal surface passageway 12 extends from the proximal surface 18 to the proximal aperture 14. In the embodiment shown, one proximal aperture 14 is provided for each proximal surface passageway 12. In alternative embodiments, a plurality of proximal surface passageways 12 may extend to a single proximal aperture 14. Alternatively, a plurality of proximal apertures 14 may lead to a single proximal surface passageway 12.

One or more distal apertures 16 are provided on an external wall 26 of the lock body 410. Each distal surface passageway 22 extends from the distal surface 20 to the distal aperture 16. In the embodiment shown, one distal aperture 16 is provided for each distal surface passageway 22. In alternative embodiments, a plurality of distal surface passageways 22 may extend to a single distal aperture 16. Alternatively, a plurality of distal apertures 16 may lead to a single distal surface passageway 22.

Generally, the diameter of each of the proximal surface passageways 12, the distal surface passageways 22, the proximal apertures 14, and the distal apertures 16 is sufficient to accommodate a suture 150. Thus, the diameter of the proximal surface passageways 12, the distal surface passageways 22, the proximal apertures 14, and the distal apertures 16 may be slightly greater than or slightly less than the outside diameter of suture 150. In one embodiment, the diameter of the proximal surface passageways 12, the distal surface passageways 22, the proximal apertures 14, and the distal apertures 16 may be between approximately 2% and approximately 50% larger or smaller than the outside diameter of the suture 150, for example approximately 33% larger or smaller than the outside diameter of the suture 150.

The lock body 410 receives a plurality of sutures 150 to fasten the filaments 8. The suture filaments are threaded through the proximal surface passageways 12 and the distal surface passageways 22. The suture filaments may be threaded through the lock body 10 in any suitable manner. For the purposes of illustration, the threading is described with first threading through the proximal surface passageways 22 and then through the distal surface passageways 22. Accordingly, a suture 150 is threaded into a proximal surface passageway 12 and out a proximal aperture 14, extended over a portion of the external wall 26, threaded into a distal aperture 16 and out a distal surface passageway 22. The proximal surface passageway 12 and the distal surface passageway 22 together allow for the translational movement of the lock body 410 with respect to the suture 150. One or more filaments 8 may be threaded through each set of proximal surface passageways 12, proximal apertures 14, distal apertures 16, and distal surface passageways 22. Again, a single proximal aperture 14 or distal aperture 16 may be provided for a plurality of proximal passageways 12 or distal passageways 22, respectively. Further, a single passageway including a proximal portion and a distal portion may be provided extending between a proximal aperture 14 and a distal aperture 16.

The positioning of the sutures 150 within the body 410 once threaded can be varied to control resistance of the sutures 150. For example, the path of the sutures 150 through the body 410 may be longer or shorter, more or less tortuous, etc. Resistance of the sutures 150 to the lock body 410 contributes to the ease of deployment of the sutures 150 and the ability of the sutures 150 to stay in place once the lock body 410 is deployed. While this is described specifically with reference to the embodiment of FIGS. 25-27, it applies to all embodiments of lock bodies discussed herein.

In the embodiment illustrated in FIGS. 25-27, the proximal surface passageway 18 and distal surface passageway 22 are aligned with respect to the radial axis (A-A of FIG. 26) of the lock body 410. In alternative embodiments, the proximal surface passageway 18 and the distal surface passageway 22 may be offset, for example by an acute angle with respect to the radial axis (A-A) of the lock body 410. This embodiment allows for more surface area over which the sutures travel which, in turn, provides more drag force.

FIG. 25 illustrates the needles 140 deployed at a vascular puncture 2 of an artery 4. In the embodiment shown, four needles 140 and associated sutures 150 are used. In alternative embodiments, any suitable number of needles 140 and/or sutures 150 may be used. The sutures 150 extend from the needle 140, through the distal surface passageway 22, through the distal aperture 14, over the external wall 26, through the proximal aperture 14, and out the proximal surface passageway 12.

After the needle 140 has been deployed but before the lock body 410 is deployed, the lock body 410 is positioned proximally of the needle 140. A pushing force is applied against the lock body 410 in the direction of the arrow (see FIG. 25) to drive the lock body 410 along the sutures 150, until the lock body 410 contacts with the vascular puncture 2, or until force is no longer applied. A pushing element may be used to apply the pushing force to the lock body 410. As described with reference to FIG. 33, a suture knot system 300 may be used to deploy the lock body 10 and to keep the sutures in tension, for example by pulling the sutures taut proximally.

The drag force or friction created by contact of each suture 150 with proximal surface passageway 12, distal surface passageway 22, and external wall 26 is sufficient to retain the lock body 410 in contact with the vascular puncture 2. However, to ensure secure positioning of the lock body 410 at the vascular puncture 2, an outer sleeve 24 may be deployed over the lock body 410. FIG. 27 illustrates the outer sleeve 24 deployed over the lock body 410. Once the lock body 410 is in contact with the vascular puncture 2, the suture sleeve 24 may be slidably placed over the lock body 410. The suture sleeve 24 is frictionally engaged with the external wall 26 of the lock body 410. This frictional engagement provides additional resistance to retain the lock body 410 in contact with the vascular puncture. The outer sleeve 24 may be sized and configured to snugly fit over the lock body 410 and sutures 150 extending over the external wall 26 of the lock body 410. In various embodiments, an outer sleeve is not used.

Figure 28:
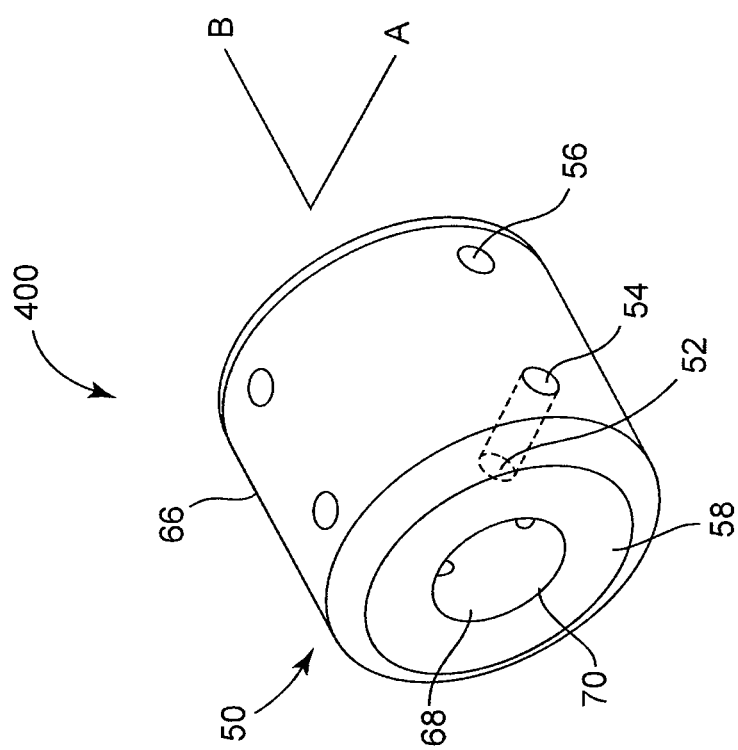
FIG. 28 illustrates a lock body of a suture attachment device in accordance with a further embodiment.
Figure 29:
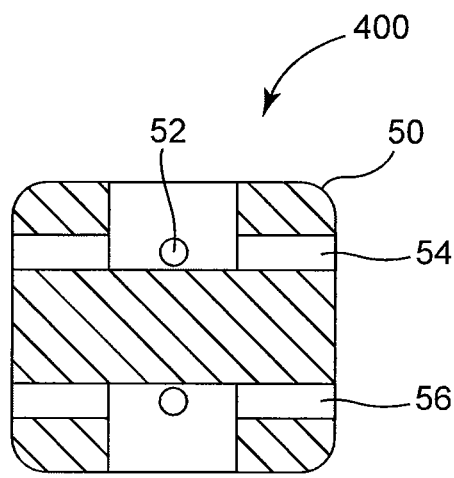
FIG. 29 illustrates a cross section of the lock body of FIG. 28.

FIGS. 28 and 29 illustrate an alternate embodiment of a suture attachment device 400. The suture attachment device 400 comprises a lock body 50. The lock body 50 may comprise a molded piece of bioabsorbable material such as a polymer. As shown, the lock body 50 is substantially cylindrical. Alternatively, the lock body 50 may be rectangular, spherical, or otherwise shaped. The lock body extends along a longitudinal axis (axis line B) which is substantially perpendicular to a radial axis (axis line A).

The lock body 50 has a proximal surface 58 (farthest away from the vascular puncture) and a distal surface 60 (closest to the vascular puncture). An internal cavity is provided within the lock body 50, extending the lock body 50 substantially along the longitudinal axis (axis line B-B). The internal cavity 68 has an internal cavity wall 70. Defined in the internal cavity wall 70 is at least one proximal passageway 52 and at least one distal passageway 62. In the embodiment shown, four proximal passageways 52 and four distal passageways 62 are provided. More or fewer proximal passageways 52 and distal passageways 62 may be provided and the number of proximal passageways 52 and the number of distal passageways 62 need not be equal.

The proximal passageway 52 terminates in a proximal aperture 54 defined in an external wall 66 of the lock body 50. In the embodiment shown, one proximal aperture 54 is provided for each proximal passageway 12. In alternative embodiments, a plurality of proximal passageways 52 may extend to a single proximal aperture 54. Alternatively, a plurality of proximal apertures 54 may lead to a single proximal passageway 52.

The distal passageway 62 terminates in a distal aperture 56 defined in the external wall 66 of the lock body 50. In the embodiment shown, one distal aperture 56 is provided for each distal passageway 62. In alternative embodiments, a plurality of distal passageways 52 may extend to a single distal aperture 56. Alternatively, a plurality of distal apertures 56 may lead to a single distal passageway 62.

Generally, the diameter of each of the proximal passageways 52, the distal passageways 62, the proximal apertures 54, and the distal apertures 56 is sufficient to accommodate a suture 150. Thus, the diameter of the proximal surface passageways 52, the distal surface passageways 62, the proximal apertures 54, and the distal apertures 56 may be slightly greater than or slightly less than the outside diameter of suture 150.

The lock body 50 receives a plurality of sutures 150 to fasten the filaments 8. The suture filaments are threaded through the proximal passageways 52 and the distal surface passageways 22. The order of threading before use is not of importance. However, for the purposes of illustration, the threading is described with first threading through the proximal passageways 52 and then through the distal passageways 62. Accordingly, a suture 150 is threaded into a proximal passageway 52 and out a proximal aperture 54, extended over a portion of the external wall 66, threaded into a distal aperture 56 and out a distal passageway 62. The proximal passageway 52 and the distal passageway 62 together allow for the translational movement of the lock body 50 with respect to the suture 150. One or more filaments 8 may be threaded through each set of proximal passageways 52, proximal apertures 54, distal apertures 56, and distal passageways 62. Again, a single proximal aperture 54 or distal aperture 56 may be provided for a plurality of proximal passageways 52 or distal passageways 62, respectively. Similarly, a single proximal passageway 52 or distal passageway 62 may be provided for a plurality of proximal apertures 54 or distal apertures 56, respectively.

The suture lock device of FIGS. 28 and 29 is deployed in the same manner as that of FIGS. 24-26. The needle 140 is deployed at a vascular puncture of an artery. Sutures 150 extend from the needle 140, through the distal passageway 62, through the distal aperture 56, over the external wall 66, through the proximal aperture 54, and out the proximal passageway 52.

After the needle 140 has been deployed but before the lock body 50 is deployed, the lock body 50 is positioned proximally of the anchor 140. As a pushing force is applied against the lock body 50 towards the vascular puncture site, the lock body 50 is driven along the sutures 150, until the lock body 50 contacts with the vascular puncture, or until force is no longer applied. This pushing force, in turn, forces the wound to come together and provides an approximate sealing of the vascular wound. Before, during, or after suture lock device deployment, the physician may apply manual compression to the surgical site to reduce bleeding. A pushing element may be used to apply the pushing force to the lock body 50.

In the embodiment illustrated in FIGS. 28 and 28, the proximal passageway 52 and distal passageway 62 are aligned with respect to the radial axis (A) of the lock body 50. In alternative embodiments, the proximal passageway 52 and the distal passageway 62 may be offset, for example by an acute angle with respect to the radial axis (A) of the lock body 50. This embodiment allows for more surface area over which the sutures travel which, in turn, provides more drag force.

Figure 30:
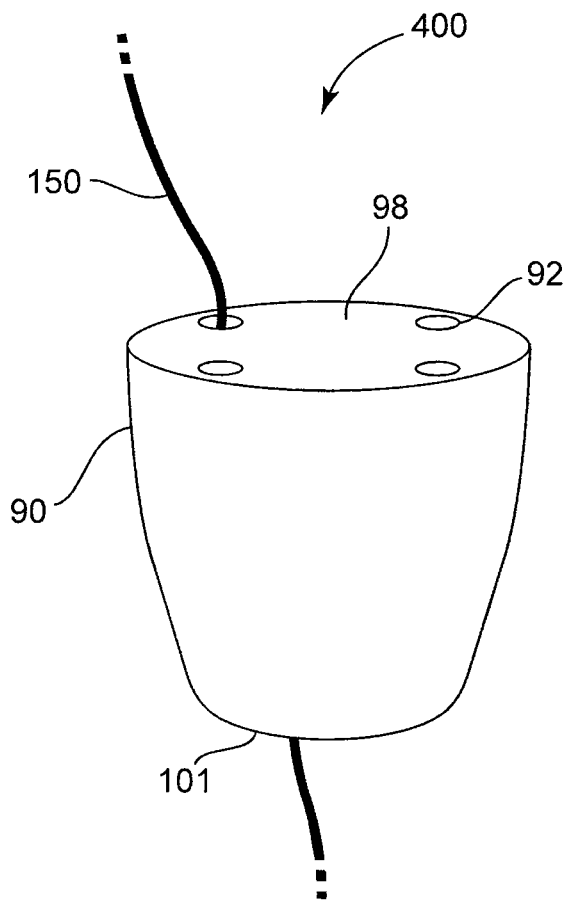
FIG. 30 illustrates lock body of a suture attachment device in accordance with yet another embodiment.
Figure 31:
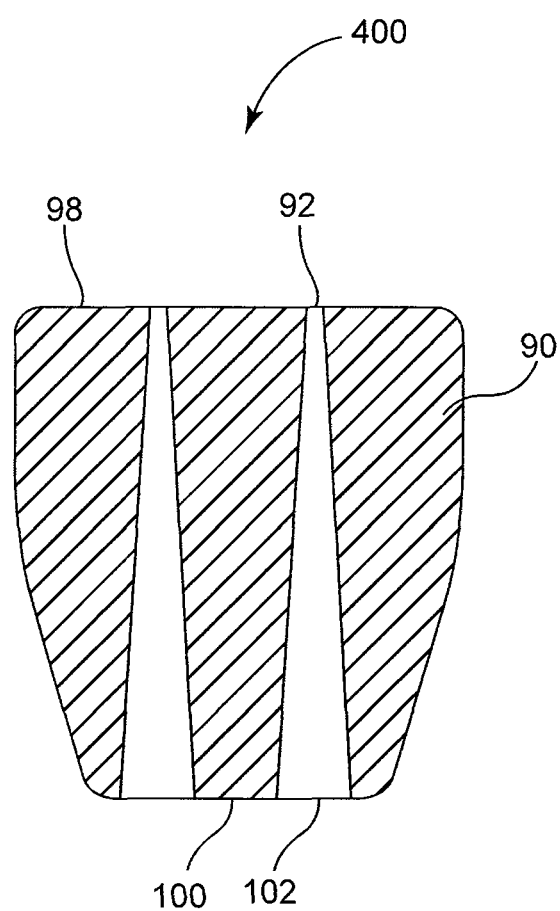
FIG. 31 illustrates a cross section of the lock body of FIG. 30.

FIGS. 30 and 31 illustrate a further embodiment of a suture lock device 400. The suture lock device 400 comprises a lock body 90. The lock body 90 may comprise a molded piece of bioabsorbable material or may alternatively comprise any suitable material manufactured in any suitable manner. As depicted in FIG. 30, the lock body 90 comprises a tapered cylinder. The cylinder tapers at its distal end (closest to the vascular puncture) to enable easy traveling into subcutaneous tissue. In alternative embodiments, the lock body 90 may not be tapered. Further, the lock body 90 may be provided in any suitable shape and may be round, flat, spherical, rectangular, or other. The lock body 90 extends along a longitudinal axis which is substantially perpendicular to a radial axis.

The lock body 90 includes a proximal surface 98 (farthest away from the vascular puncture) and a distal surface 100 (closest to the vascular puncture). At least one proximal surface passageway 92 is provided on the proximal surface 98 while at least one distal surface aperture 102 is provided on the distal surface 100. As shown, each proximal surface passageway 92 extends to a corresponding distal surface aperture 102. In the embodiment illustrated in FIG. 30, there are four proximal surface passageways 92 and four distal surface apertures 102. In alternative embodiments, more or fewer proximal surface passageways 92 and more or fewer distal surface apertures 102 may be provided. Further, the number of proximal surface passageways 92 and the number of distal surface apertures 102 need not be equal. Thus, for example, a plurality of proximal surface passageways 92 may terminate in a single distal surface aperture 102. FIG. 31 illustrates a schematic cross section of the suture lock device 90. As shown, each proximal surface passageway 92 terminates in a distal surface aperture 102.

Generally, the diameter of each of the proximal surface passageways 92 and the distal surface apertures 102 is sufficient to accommodate a suture 150. Thus, the diameter of the proximal surface passageways 92 and the distal surface apertures 102 may be slightly greater than the outside diameter of suture 150. As shown, the diameter of the proximal surface passageway 92, however, increases as it passes through the suture lock device 90, terminating in a maximum diameter at distal surface aperture 102.

The suture lock device of FIGS. 30 and 31 is deployed in the same manner as that of FIGS. 25-27. The needle 140 is deployed at a vascular puncture of an artery. Sutures 150 extend from the needle 140, through the distal surface aperture 62 and out the proximal surface passageway 92. After the needle 140 has been deployed but before the lock body 90 is deployed, the lock body 90 is positioned proximally of the anchor. As a pushing force is applied against the lock body 90 towards the vascular puncture site, the lock body 90 is driven along the sutures 150, until the lock body 90 contacts with the vascular puncture, or until force is no longer applied. A pushing element may be used to apply the pushing force to the lock body 90.

The proximal surface passageways 92 allow for the translational movement of the suture lock device 90 with respect to the suture 150. Once the suture lock device 90 is in contact with a vascular puncture, the drag force created by contact of suture 150 with proximal passageway 92 is sufficient to retain the suture lock device 90 in contact with the vascular puncture.

Figure 32:
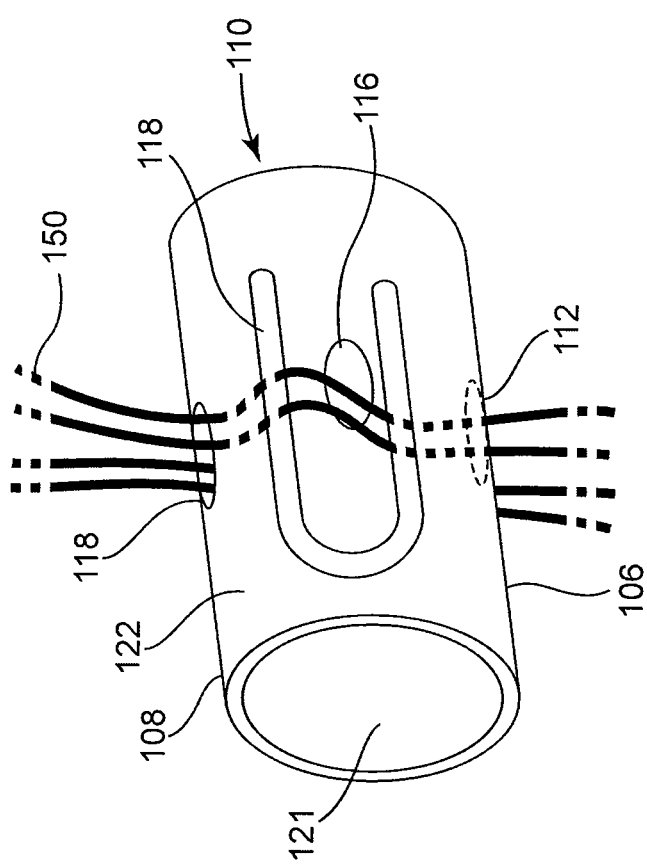
FIG. 32 illustrates a suture attachment device in accordance with yet a further embodiment.
Figure 33:
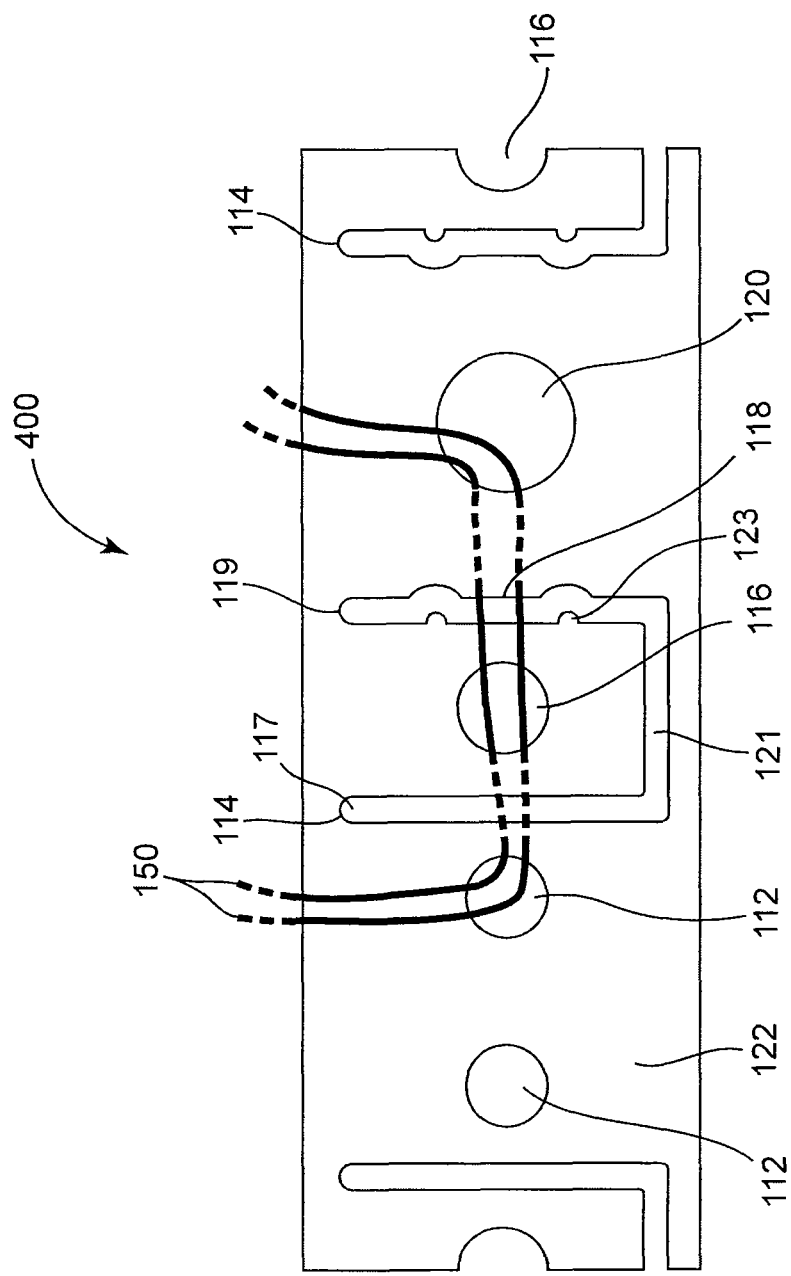
FIG. 33 illustrates a flattened view of the suture attachment device of FIG. 32.
Figure 34:
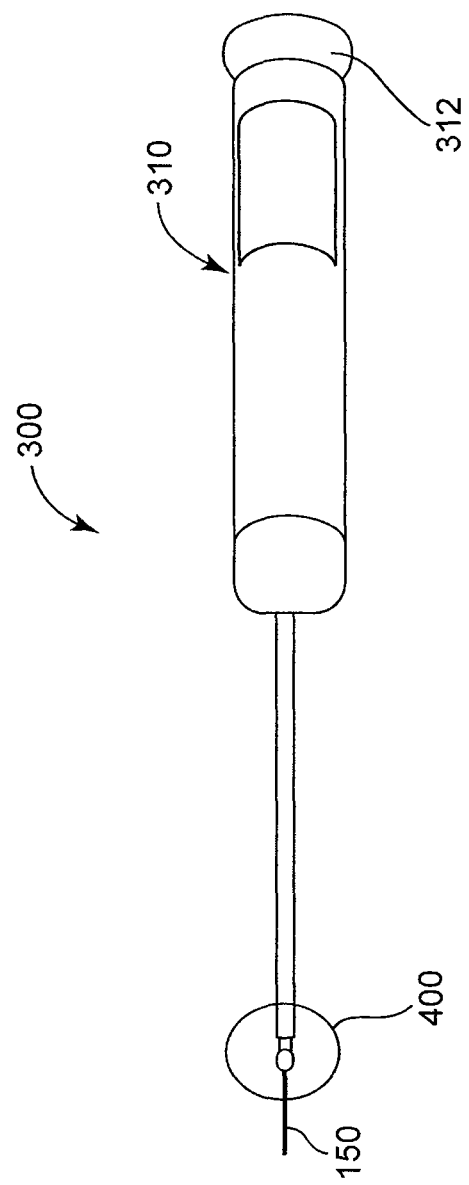
FIG. 34 illustrates a suture knot system in accordance with one embodiment.

Referring to FIGS. 32 and 33, a further embodiment of a suture lock device 400 is illustrated. FIG. 32 illustrates the suture lock device 400 as deployed. FIG. 33 illustrates a "rolled out" version of the suture lock device 400 for purposes of illustration.

The suture lock device 400 includes a base element 122 comprising one or more crimping means 114. As shown, the crimping means 114 are integral to the base element 122. As shown in FIG. 31, the base element 122 is substantially tubular and cylindrical, having a distal side 106 and a proximal side 108. When deployed, the proximal side 108 is nearest to the vascular puncture while the distal side 106 is farthest from the vascular puncture. In alternative embodiments, the base element may be any suitable shape, for example, the base element may be rectangular or spherical. The base element 122 extends along a longitudinal axis substantially perpendicular to a radial axis. The base element 122 includes an internal cavity 125 that extends through the device along the longitudinal axis.

A plurality of entrance apertures 112 and an exit aperture 121 are provided along the base element 122. The entrance apertures 112 are positioned along the proximal side 108 of the suture lock device 400 and the exit aperture 121 is positioned along the distal side 106 of the suture lock device 400 when deployed.

In the embodiment shown, two crimping means 114 are provided. Each crimping means comprises a suture clip 115, and a crimping slot 118 defined between the suture clip 115 and the base element 122. As shown, the suture clip 115 is a portion of the base element 122 cut along three walls 117, 117a and hinged along the fourth 119. Two notches 123 are provided along one wall 117a of the suture clip 115 to aid in preventing longitudinal migration of the sutures 8. The notches 123 maintain the sutures in a central position of the suture clip, as described more fully below. In alternative embodiments, the suture clip 115 may not be integral with the base element 122. Thus, for example, a portion of the base element 122 may be cut away and a separate suture clip 115 fixedly secured to the base element 122. A suture aperture 116 is provided on each suture clip 115.

Two pairs of sutures are threaded through the suture lock device 400. A first pair of sutures 8 is threaded into the central cavity 125 of the suture lock device 400 through a first entrance aperture 112a. The sutures 8 are extended under a first portion of the first suture clip 115a and threaded out through the suture aperture 116 of the suture clip. The sutures 8 are then threaded through the crimping slot 118 along wall 117a between notches 123, thereby reentering the central cavity 125. The sutures 8 are then threaded within the central cavity 125 to exit through the exit aperture 121.

Similarly, a second pair of sutures 8 is threaded into the central cavity 125 of the suture lock device 400 through a second entrance aperture 112b. The sutures 8 are extended under a first portion of the second suture clip 115b and threaded out through the suture aperture 116 of the suture clip. The sutures 8 are then threaded through the crimping slot 118 along wall 117a between notches 123, thereby reentering the central cavity 125. The sutures 8 are then threaded within the central cavity to exit trough the exit aperture 121.

The entrance apertures 112, suture apertures 116, crimping slots 118, and exit aperture 121 allow for the translational movement of the suture lock device 400 with respect to the sutures 150. The frictional engagement of the sutures with the suture lock device 100 is sufficient to retain the suture lock device 100 in contact with the vascular puncture. While the embodiment of FIGS. 31 and 32 is described specifically with reference to two pairs of suture filaments, it is to be appreciated than any suitable number of suture filaments may be used and even numbers of suture filaments are not necessary.

FIG. 34 illustrates one embodiment of the suture knot system 300 including a suture lock device 400. As shown, the suture knot system includes a suture portion 5 includes an outer shaft 10 having a distal end 15 and a proximal end 20 and a handle 310. The handle 310 may include a tensioning knot for adjusting tension of the suture 150. The suture lock device 400 is provided over the sutures 150 at the distal end 15 of the outer shaft 10 of the suture portion 5. The suture knot system 300 may be used to deploy the suture lock device 400. As discussed previously, sutures 150 extend from the surgical site, through the suture portion 5 and, optionally, through the handle 300 to the tensioning knob 312. The sutures 150 travel through the handle 300 and the handle 300 acts as a pusher to push the suture lock device 400 to the surgical site. This engagement keeps the sutures 150 substantially in tension while the suture lock device 400 is being deployed. The tensioning knob 312 may additionally be pulled or actuated to affirmatively tense the sutures 150. By keeping the sutures substantially in tension during suture lock device deployment, slack in the sutures between the suture site and the suture lock device as deployed is substantially avoided.

Figure 35:
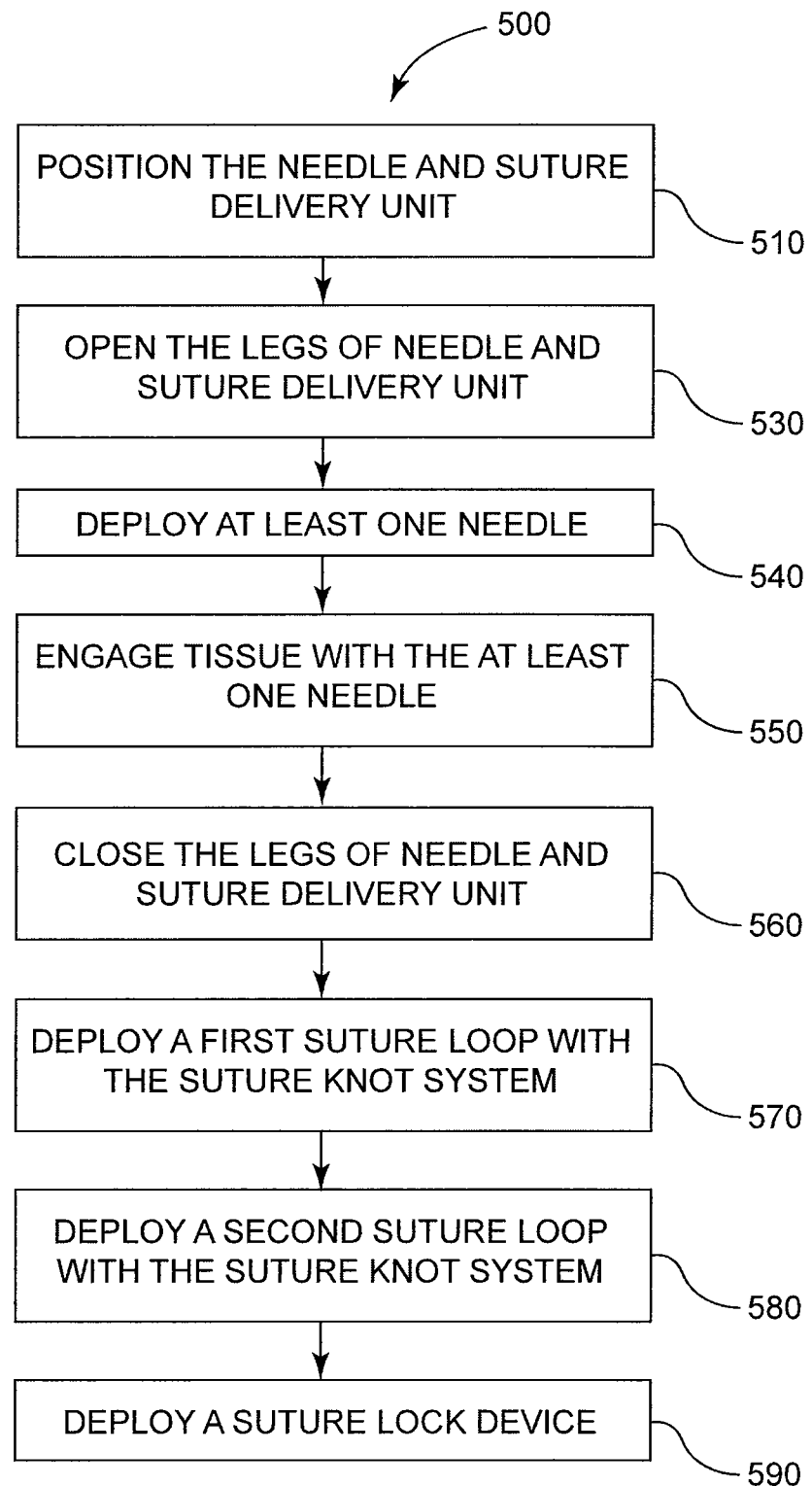
FIG. 35 illustrates a method of using the vascular closure delivery system in accordance with one embodiment.

FIG. 35 illustrates one embodiment of a method 500 of using the vascular closure delivery system. The method 500 includes positioning 510 the needle and suture delivery unit, opening 530 the legs of the needle and suture delivery unit, deploying 540 the needles, engaging 550 tissue with the needles, deploying 570 a first suture loop, deploying 580 a second suture loop, and deploying 590 the suture lock device.

Positioning 510 the needle and suture delivery unit may comprise positioning the needle and suture delivery unit in a lumen using a locator. Using a standard locator, when blood no longer flows through the locator, the correct location has been established. The needle and suture delivery unit may be covered using a sheath. If covered, the suturing assembly is exposed before deploying the needle and suture. Such exposure may be by retracting the sheath. If not covered, the suturing assembly is exposed as positioned.

The suturing assembly is opened 530 such that the position of components of the suturing assembly is suitable for needle deployment. In one embodiment, opening 530 comprises opening legs of the suturing assembly. In one embodiment, the legs are moved to an open position by deploying a pull force on an actuator disposed on the handle. The pull force pulls the needle deployment tubes proximally, thereby pulling the tubes and legs from their collapsed state to an operational and open position. Tactile feedback may indicate to the user to stop applying pull force when the legs have opened. In the open position, the legs are generally perpendicular to the support and are flexibly suspended via a tensioning device which may be located at the handle of the delivery unit. In some embodiments, the suturing assembly may be positioned 510 in an open configuration such that no further opening is necessary.

Deploying 540 the needles may comprises expelling the needles from the needle delivery tubes by, for example, advancing the pushers. In one embodiment, such delivery is performed by releasing a push button actuator on the handle. The actuator is actuated to deploy the pushers. Such actuation may comprise depressing a push button. The pushers may be deployed directly or via an actuating member. Further, the pushers may be deployed proximally or distally depending on the orientation of the needle and suture delivery unit. The pushers deploy 540 the needles from the expulsion end of the needle carrier tubes. The expulsion end of the needle carrier tubes may be proximal or distal depending on the orientation of the needle and suture delivery unit.

After needle deployment, the pushers are retracted. In one embodiment, deployment of the needles is via actuation of a flywheel. The flywheel moves the pushers to deploy the needles. Such movement of the pushers may be via an actuating member. Continued movement of the flywheel causes the pushers to retract. As the pushers retract, the needles engage 550 tissue. Engagement of the tissue prevents the needles from retracting with the pushers.

After the suturing assembly has deployed the needles, the needle and suture delivery unit may be closed 560, for example by returning the legs to the closed configuration. In some embodiments, it may not be necessary to close the suturing assembly. The suturing assembly may then removed from the lumen.

Using the suture knot system, first and second overhand loops are moved to the surgical site. A pushing force is applied to the suture portion of the suture knot system to drive the knots distally toward the surgical site until the distal end of the suture portion contacts the surgical site, or until force is no longer applied. When the suture portion contacts the surgical site, the first suture loop may be deployed 570. The first suture loop approximates the wound lips and seals the surgical site. Upon contact of the suture portion with the surgical site, the second overhand suture loop may also be deployed 580 at the surgical site. The second suture loop secures the sealing result of the first suture loop, tightens the knot, and minimizes any loosening of the knot under pulsation.

A lock body is deployed 590 over the sutures. The lock body may be deployed after knots have been advanced over the sutures, may be deployed before knots are advanced over the suture, or may be deployed in lieu of knots. To deploy the lock body, a pushing force is applied against the lock body to drive the lock body along the sutures until the lock body contacts the vascular puncture or until force is no longer applied. An outer sleeve may be deployed over the lock body.

The sutures may then be cut and the suture knot system removed.

Although the present invention has been described with reference to preferred embodiments, persons skilled in the art will recognize that changes may be made in form and detail without departing from the spirit and scope of the invention.

What is claimed is:

1. A vascular closure device having a proximal end proximate to a user and a distal end, comprising:
   a support member;
   a leg having first and second ends, the first end being pivotally mounted to the support member, the leg being movable between a stowed position and a deployed position;
   a needle carrier tube connected to the second end of the leg and having an open end facing proximally in both the stowed position and the deployed position;
   a needle positioned in the needle carrier tube;
   a pusher positioned in the needle carrier tube at a location distal of the needle and operable to advance the needle out of the open end of the needle carrier tube when the leg is in the deployed position;
   wherein the leg and the needle carrier tube are axially aligned with the support member when the leg is in the stowed position, and the leg and needle carrier tube are arranged out of alignment with the support member when the leg is in the deployed position.

2. The vascular closure device of claim 1, further comprising a tensioning member operable to move the leg between the stowed and deployed positions.

3. The vascular closure device of claim 1, further comprising a plurality of legs and a plurality of needle carrier tubes, the first end of each of the plurality of legs being pivotally mounted to the support member, the second end of each of the plurality of legs being connected to a separate one of the plurality of needle carrier tubes, and a separate needle and pusher being positioned within each of the plurality of needle carrier tubes.

4. The vascular closure device of claim 1, further comprising a suture connected to the needle and extending from the open end of the needle carrier tube.

5. The vascular closure device of claim 4, wherein the support member comprises a hollow shaft, and the suture extends through the hollow shaft to the needle.

6. The vascular closure device of claim 1, wherein the needle includes a sharp end arranged facing the pusher.

7. The vascular closure device of claim 1, wherein the needle includes a sharp end arranged facing proximally toward the open end of the needle carrier tube.

8. The vascular closure device of claim 1, wherein the leg and needle carrier tube are aligned in parallel with the support member when the leg is in the stowed position.

9. The vascular closure device of claim 1, further comprising an actuator operable to move the pusher proximally within the needle carrier tube.

10. The vascular closure device of claim 1, further comprising a handle, the support member extending distally from the handle, and the actuator being mounted to the handle.

11. The vascular closure device of claim 1, wherein the needle extends through a portion of the leg.

12. A vascular closure device having a proximal end proximate to a user and a distal end, comprising:
a handle;
a hollow shaft extending distally from the handle;
a leg having first and second ends, the first end being connected to the hollow shaft, the leg being movable between a stowed position and a deployed position;
a needle carrier tube connected to and extending distally from the second end of the leg and having an open end facing proximally in both the stowed position and the deployed position;
a needle positioned in the needle carrier tube and having a sharp end facing proximally toward the handle;
a pusher disposed in the needle carrier tube, the pusher operable to advance the needle out of the needle carrier tube in a proximal direction;
wherein the leg and the needle carrier tube are axially aligned with the hollow shaft when the leg is in the stowed position, and the leg and needle carrier tub are arranged out of alignment with the hollow shaft when the leg is in the deployed position.

13. The vascular closure device of claim 12, wherein the leg and the needle carrier tube are axially aligned when the leg is in the stowed position, and the leg and needle carrier tube are arranged out of alignment when the leg is in the deployed position.

14. The vascular closure device of claim 12, further comprising an actuator mounted to the handle and coupled to the pusher to operate the pusher.

15. The vascular closure device of claim 12, further comprising a suture connected to the needle and extending through the hollow shaft.

16. The vascular closure device of claim 12, further comprising an inner tubular member positioned in the hollow shaft and being rotatable relative to the hollow shaft to control release of the suture.

17. The vascular closure device of claim 12, further comprising a rod axially movable within the inner tubular member to advance the suture out of the hollow shaft.

18. The vascular closure device of claim 12, further comprising a tensioning member coupled to the leg to move the leg between the stowed and deployed positions.

19. The vascular closure device of claim 12, wherein the leg and needle carrier tube are arranged in parallel with the hollow shaft when the leg is in the stowed position and are arranged out of alignment relative to the hollow shaft when the leg is in the deployed position.

20. The vascular closure device of claim 12, further comprising an inner tubular member positioned in the hollow shaft and being rotatable relative to the hollow shaft to control release of the suture.

* * * * *